(12) United States Patent
Nagai

(10) Patent No.: US 10,408,681 B2
(45) Date of Patent: Sep. 10, 2019

(54) SPECTROCOLORIMETRIC DEVICE AND SPECTRAL REFLECTANCE CALCULATING METHOD

(71) Applicant: KONICA MINOLTA, INC., Chiyoda-ku (JP)

(72) Inventor: Yoshiroh Nagai, Nishinomiya (JP)

(73) Assignee: KONICA MINOLTA, INC., Tokyo (JP)

( * ) Notice: Subject to any disclaimer, the term of this patent is extended or adjusted under 35 U.S.C. 154(b) by 8 days.

(21) Appl. No.: 15/571,376

(22) PCT Filed: Apr. 13, 2016

(86) PCT No.: PCT/JP2016/061916
§ 371 (c)(1),
(2) Date: Nov. 2, 2017

(87) PCT Pub. No.: WO2016/181746
PCT Pub. Date: Nov. 17, 2016

(65) Prior Publication Data
US 2018/0356286 A1  Dec. 13, 2018

(30) Foreign Application Priority Data

May 14, 2015 (JP) ................................ 2015-099295

(51) Int. Cl.
*G01J 3/50* (2006.01)
*G01N 21/55* (2014.01)
*G01J 3/52* (2006.01)

(52) U.S. Cl.
CPC .............. *G01J 3/502* (2013.01); *G01J 3/524* (2013.01); *G01N 21/55* (2013.01)

(58) Field of Classification Search
CPC .... G01J 3/502; G01J 3/02; G01J 3/50; G01N 21/55
See application file for complete search history.

(56) References Cited

U.S. PATENT DOCUMENTS 5,369,494 A   11/1994  Bowden et al.
7,650,093 B2   1/2010  Suzuki
(Continued)

FOREIGN PATENT DOCUMENTS

JP   61-292026   12/1986
JP   61-292043   12/1986
(Continued)

OTHER PUBLICATIONS

A. Ingleson et al., "Methods of Selecting a Small Reflectance Set as a Transfer Standard for Correcting Spectrophotometers", © 2005 Wiley Periodicals, Inc., vol. 31, No. 1, Feb. 2006.

*Primary Examiner* — Hina F Ayub
(74) *Attorney, Agent, or Firm* — Cozen O'Connor

(57) ABSTRACT

In order to provide a technique by which a highly-accurate conversion rule of measurement values between different spectrocolorimetric devices can be easily set, the spectrocolorimetric device includes a light source, a light-receiving unit, and a conversion unit. The light-receiving unit spectroscopically disperses reflected light generated on a surface of an object according to irradiation of the object with illumination light emitted from the light source and measures a spectroscopic spectrum of the reflected light. The conversion unit calculates a spectral reflectance that can be acquired by another spectrocolorimetric device from the spectroscopic spectrum by using a calibrated spectral sensitivity of the other spectrocolorimetric device different from the spectrocolorimetric device and the spectroscopic spectrum.

7 Claims, 20 Drawing Sheets

(56) References Cited

U.S. PATENT DOCUMENTS

| | | | |
|---|---|---|---|
| 8,755,701 B2 | 6/2014 | Hyoki | |
| 2006/0290929 A1* | 12/2006 | Imura | G01J 3/02 |
| | | | 356/328 |
| 2011/0128540 A1 | 6/2011 | Iida et al. | |
| 2012/0296595 A1* | 11/2012 | Dalal | G01J 3/501 |
| | | | 702/104 |
| 2013/0038867 A1* | 2/2013 | Ebihara | G01J 3/502 |
| | | | 356/300 |
| 2013/0050703 A1 | 2/2013 | Colman | |

FOREIGN PATENT DOCUMENTS

| | | |
|---|---|---|
| JP | 62-289736 | 12/1987 |
| JP | 2006-177813 | 7/2006 |
| JP | 2009-008561 | 1/2009 |
| JP | 2010-085327 | 4/2010 |
| JP | 2011-107114 | 6/2011 |
| JP | 2011-133463 | 7/2011 |
| JP | 2013-160555 | 8/2013 |

* cited by examiner

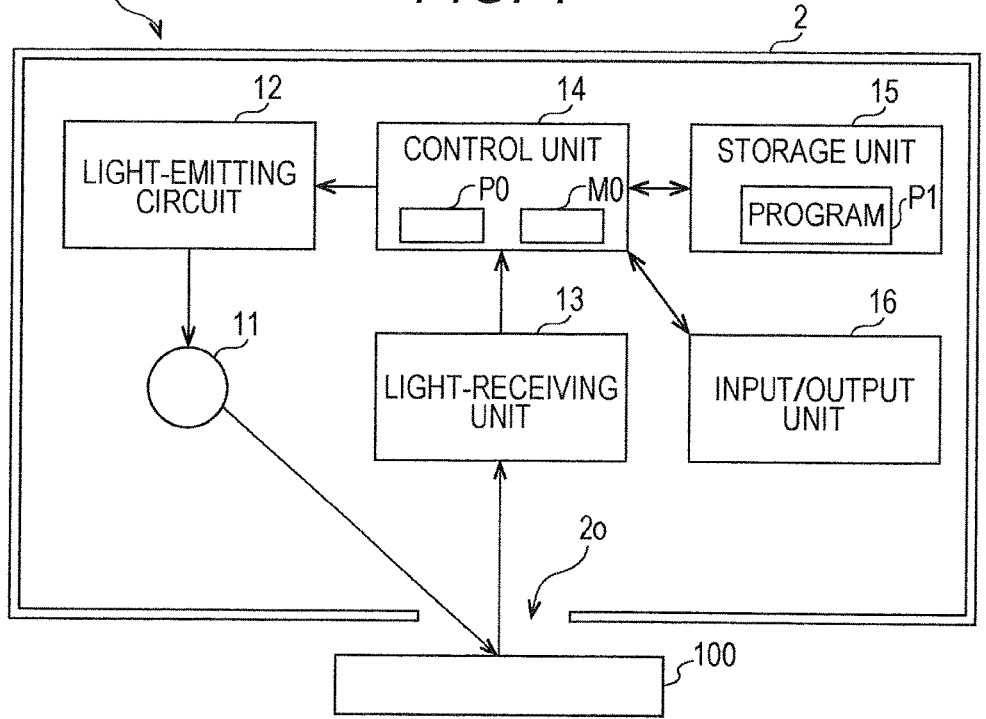
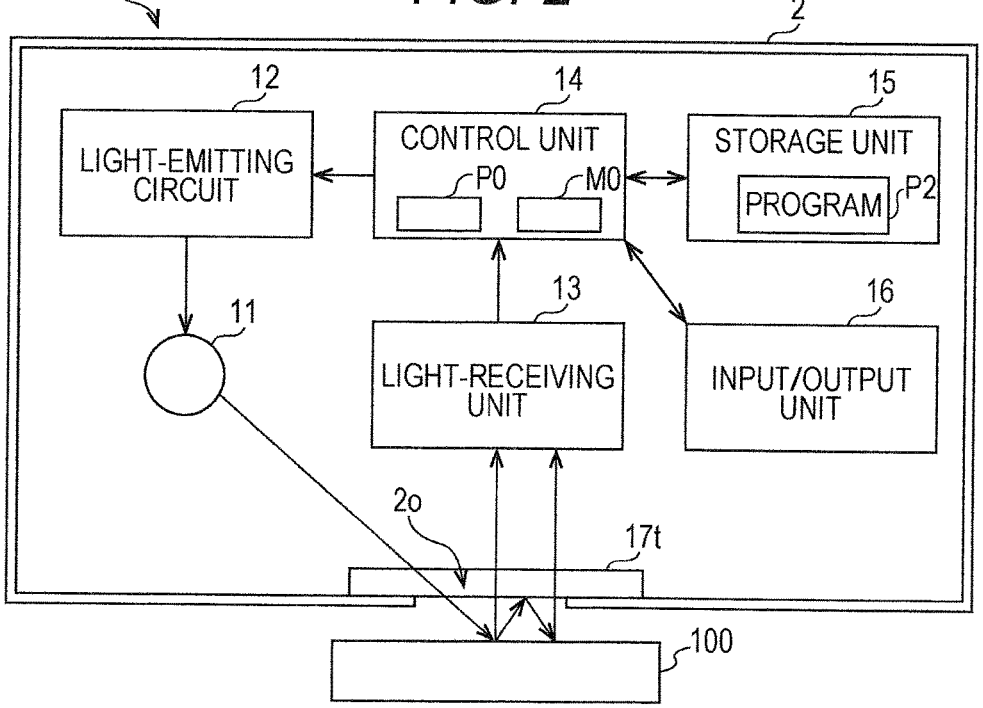

SPECTROCOLORIMETRIC DEVICE AND SPECTRAL REFLECTANCE CALCULATING METHOD

RELATED APPLICATIONS

This is a U.S. National Phase Application under 35 USC 371 of International Application PCT/JP2016/061916 filed on Apr. 13, 2016.

This application claims the priority of Japanese application no. 2015-099295 filed May 14, 2015, the entire content of which is hereby incorporated by reference.

TECHNICAL FIELD

The present invention relates to a spectrocolorimetric device and a spectral reflectance calculating method.

BACKGROUND ART

In recent years, in order to manage finishing of a surface color of an object, a spectrocolorimetric device for measuring a spectral reflectance on a surface of the object is used (for example, Patent Literatures 1 to 3, or the like). In the spectrocolorimetric device, for example, by using measurement values relating to black chromacity and white chromacity obtained by measurement of two standard colors of black and white, a measurement value relating to the spectral reflectance of the object can be calibrated (for example, Patent Literature 1, or the like).

With respect to such spectrocolorimetric devices, for example, a plurality of spectrocolorimetric devices are used in parallel in a factory or the like, and some of the spectrocolorimetric devices are replaced with new spectrocolorimetric devices, so that a usage situation in which plural types of the spectrocolorimetric devices can coexist can be assumed. As a mode of replacing the spectrocolorimetric devices, for example, there is a mode in which a spectrocolorimetric device that has been used up to now is replaced with a succeeding model of the spectrocolorimetric device.

In this usage situation, if measurement values of two standard colors of black and white are used and the measurement values relating to the object are calibrated, with respect to objects close to black and white, even though the same object is measured by different spectrocolorimetric devices, similar spectral reflectances can be obtained. On the other hand, since calibration methods relating to the optical system and spectral sensitivity are different between different models or between devices manufactured by different manufacturers, if objects of colors different from black and white are measured by different spectrocolorimetric devices, different spectral reflectances can be acquired for different spectrocolorimetric devices.

Therefore, a method of converting a spectral reflectance $R_m(i)$ obtained by measurement of a certain object with a spectrocolorimetric device m to a spectral reflectance $R_t(i)$ obtained by measurement of the same object with another spectrocolorimetric device t by Mathematical Formula (1) is proposed (for example, Non Patent Literature 1 or the like). In Mathematical Formula (1), λ denotes a wavelength, and A(i), B(i), C(i), D(i), and E(i) denote coefficients of the first to fifth terms of the right hand side with respect to each i-th wavelength λ.

[Mathematical Formula 1]

$$R_t(i) = A(i) + B(i) \cdot R_m(i) + C(i) \cdot \frac{dR_m(i)}{d\lambda} + D(i) \cdot \frac{d^2 R_m(i)}{d\lambda^2} + E(i) \cdot R_m(i) \cdot (100 - R_m(i)) \quad (1)$$

In this method, the spectral reflectances acquired by actually measuring a plurality of calibration samples with the spectrocolorimetric device m and the spectrocolorimetric device t are applied to Mathematical Formula (1), so that the coefficients A(i), B(i), C(i), D(i), and E(i) of Mathematical Formula (1) are obtained. By using Mathematical Formula (1) to which the obtained coefficients A(i), B(i), C(i), D(i), and E(i) are applied, the spectral reflectance $R_t(i)$ which is to be acquired by measurement using the spectrocolorimetric device t can be calculated from the spectral reflectance $R_m(i)$ which can be acquired by measurement for any object using the spectrocolorimetric device m.

CITATION LIST

Patent Literature

Patent Literature 1: JP 61-292026 A
Patent Literature 2: JP 61-292043 A
Patent Literature 3: JP 62-289736 A

Non Patent Literature

Non Patent Literature 1: A. Ingleson and M. H. Brill, "Methods of Selecting a Small Reflectance Set as a Transfer Standard for Correcting Spectrophotometers", Color Res. Appl. 31 (2006), 13-17.

SUMMARY OF INVENTION

Technical Problem

On the other hand, for example, the spectral reflectance is illustrated by a two-dimensional graph where the horizontal axis denotes a wavelength in reflected light from an object and the vertical axis denotes a reflectance according to an intensity (or optical energy) of the reflected light from the object. For this reason, a deviation in the spectral reflectance between the different spectrocolorimetric devices may occur in two axial directions of the horizontal axial direction relating to the wavelength and the vertical axial direction relating to the optical energy. Referring to Mathematical Formula (1), the problem of linearity where the relationship between the intensity of the reflected light from the object and the measurement value for each light-receiving element of the spectrocolorimetric device is deviated from a proportional relationship may cause an error in the coefficient E(i) of the fifth term of the right hand side. In addition, the deviation relating to the wavelength of the reflected light received by each light-receiving element of the spectrocolorimetric device causes an error in the coefficient C(i) of the third term on the right hand side of Mathematical Formula (1). Further, a deviation in the full width at half maximum of the spectral sensitivity of each light-receiving element corresponding to each wavelength of the spectrocolorimetric device can cause an error in the coefficient D(i) of the fourth term on the right hand side of Mathematical Formula (1).

Herein, the coefficients A(i) to E(i) employ different values for different wavelengths λ(i). For this reason, for each wavelength λ(i), when spectral reflectances of five or more types of calibration samples of which a spectral reflectance $R_m(i)$ and a first derivative $(dR_m(i)/d\lambda)$ and a second derivative $(d^2R_m(i)/d\lambda^2)$ of the spectral reflectance $R_m(i)$ have values other than zero are actually measured, five coefficients $A(i)$ to $E(i)$ can be obtained for each wavelength $\lambda(i)$.

For example, when a calibration sample of which the spectral reflectance $R_m(i)$ has a slope with respect to the change of the wavelength $\lambda(i)$ for each wavelength $\lambda(i)$ (referred to as a detection wavelength) at which the intensity of the reflected light is detected in the spectrocolorimetric device is used, the third term on the right hand side including the first derivative $(dR_m(i)/d\lambda)$ of the spectral reflectance $R_m(i)$ in Mathematical Formula (1) has a value different from zero. In addition, for example, when a calibration sample of which slope of the spectral reflectance $R_m(i)$ is changed with respect to the change of the detection wavelength $\lambda(i)$ is used for each detection wavelength $\lambda(i)$ of the spectrocolorimetric device, the fourth term on the right hand side including the second derivative $(d^2R_m(i)/d\lambda^2)$ of the spectral reflectance $R_m(i)$ in Mathematical Formula (1) has a value different from zero.

Therefore, if a calibration sample of which the spectral reflectance $R_m(i)$, the slope of the spectral reflectance $R_m(i)$, and a change in the slope of the spectral reflectance $R_m(i)$ are large is used for each detection wavelength $\lambda(i)$, the coefficients $A(i)$ to $D(i)$ can be obtained at a good accuracy. In addition, the fifth term on the right hand side is a quadratic function which becomes the minimum at the spectral reflectance $R_m(i)$ of 0% and 100% and becomes the maximum at the spectral reflectance $R_m(i)$ of 50%. For this reason, when a plurality of calibration samples exhibiting a plurality of spectral reflectances $R_m(i)$ ranging from 0% to 100% are employed for each detection wavelength $\lambda(i)$, the coefficient $E(i)$ can be obtained at a good accuracy.

However, in a calibration sample of which the slope of the spectral reflectance $R_m(i)$ at a certain detection wavelength $\lambda(i)$ is large, the slope of the spectral reflectance $R_m(i)$ is likely to be decreased at a different detection wavelength $\lambda(i)$. For this reason, for each detection wavelength $\lambda(i)$, the optimum calibration sample for obtaining the coefficients $A(i)$ to $E(i)$ will be different. Therefore, in order to obtain the coefficients $A(i)$ to $E(i)$ for each wavelength $\lambda(i)$, a very large number of calibration samples are required. In addition, depending on a method of selecting the calibration sample, the robustness with respect to the calculation of the spectral reflectance $R_t(i)$ using Mathematical Formula (1) is different. Namely, when an error relating to measurement according to the method of selecting the calibration sample is added to one or more terms on the right hand side of Mathematical Formula (1), the spectral reflectance $R_t(i)$ calculated using Mathematical Formula (1) is likely to have an error.

In addition, in the spectrocolorimetric device, the measurement value relating to the spectral reflectance $R_m(i)$ is output at a preset predetermined wavelength interval such as an interval of 10 nm or the like. For this reason, in the actual calculation, the first derivative $(dR_m(i)/d\lambda)$ of the spectral reflectance $R_m(i)$ at the detection wavelength $\lambda(i)$ is not a value (also referred to as a differential value) of the differential of the spectral reflectance $R_m(i)$ but a value (also referred to as a difference value) of the difference of the spectral reflectance $R_m(i)$. As a result, the error due to the difference between the differential value and the difference value causes an error between the spectral reflectance $R_t(i)$ relating to the spectrocolorimetric device t obtained by the conversion using Mathematical Formula (1) from the spectral reflectance $R_m(i)$ obtained by the spectrocolorimetric device m and the spectral reflectance $R_t(i)$ obtained by actual measurement using the spectrocolorimetric device t.

In this manner, in order to realize the conversion from the spectral reflectance $R_m(i)$ to the spectral reflectance $R_t(i)$ by using Mathematical Formula (1), a large number of calibration samples are first required. In addition, it takes a long time to perform the measurement using a large number of the calibration samples. Furthermore, it is not easy to secure a conversion accuracy (robustness) depending on a method of selecting the calibration sample. Namely, complicated manipulations or operations are required for setting a rule (also referred to as a conversion rule) for converting the spectral reflectance $R_m(i)$ into the spectral reflectance $R_t(i)$, and thus, it is not easy to set the conversion rule at a high accuracy.

These problems are not limited between spectrocolorimetric devices of different manufacturers or between different models of spectrocolorimetric devices, but these problems may also occur between different spectrocolorimetric devices of the same model, and thus, these problems may generally occur between different spectrocolorimetric devices.

In view of the above problems, the present invention is to provide a technique by which a highly-accurate conversion rule of measurement values between different spectrocolorimetric devices can be easily set.

Solution to Problem

In order to solve the above problem, a spectrocolorimetric device according to one aspect includes a light source, a light-receiving unit, and a conversion unit. Herein, the light-receiving unit spectroscopically disperses reflected light generated on a surface of an object according to irradiation of the object with illumination light emitted from the light source and measures a spectroscopic spectrum of the reflected light. In addition, the conversion unit calculates a spectral reflectance that can be acquired by another spectrocolorimetric device from the spectroscopic spectrum by using a calibrated spectral sensitivity of the other spectrocolorimetric device different from the spectrocolorimetric device and the spectroscopic spectrum.

A spectral reflectance calculating method according to another aspect includes steps (a) and (b). Herein, in step (a), a light-receiving unit of a first spectrocolorimetric device spectroscopically disperses reflected light generated on a surface of an object according to irradiation of the object with illumination light emitted from a light source and measures a spectroscopic spectrum of the reflected light. In step (b), a conversion unit of the first spectrocolorimetric device calculates a spectral reflectance that can be acquired by a second spectrocolorimetric device different from the first spectrocolorimetric device from the spectroscopic spectrum by using a calibrated spectral sensitivity of the second spectrocolorimetric device and the spectroscopic spectrum measured in the step (a).

Advantageous Effects of Invention

According to the spectrocolorimetric device according to one aspect, since the calibrated spectral sensitivity with respect to the deviation relating to the spectral sensitivity is set separately from the deviation relating to the linearity of the reflectance, a highly-accurate conversion rule of measurement values between the different spectrocolorimetric devices can be easily set.

According to the spectral reflectance calculating method according to another aspect, since the calibrated spectral sensitivity with respect to the deviation relating to the spectral sensitivity is set separately from the deviation relating to the linearity of the reflectance, a highly-accurate conversion rule of measurement values between the different spectrocolorimetric devices can be easily set.

BRIEF DESCRIPTION OF DRAWINGS

FIG. 1 is a diagram schematically illustrating a configuration example of a first spectrocolorimetric device.

FIG. 2 is a diagram schematically illustrating a configuration example of a second spectrocolorimetric device.

DESCRIPTION OF EMBODIMENTS

Figure 3:
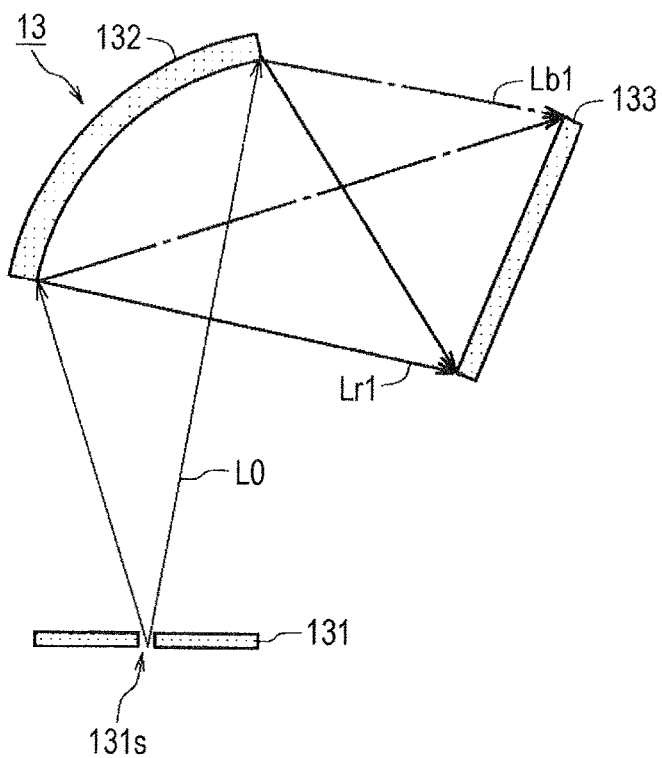
FIG. 3 is a diagram schematically illustrating a configuration example of a light-receiving unit.

Hereinafter, an embodiment of the present invention and various modified examples are described with reference to the drawings. In addition, in the drawings, components having the same configuration and function are denoted by the same reference numerals, and redundant description thereof is omitted. In addition, the drawings are schematically illustrated, and the sizes, positional relationships, and the like of the various structures in each figure can be appropriately changed.

(1) Embodiment

<(1-1) Outline of Embodiment>

For example, between different spectrocolorimetric devices, even though an object of colorimetry (also referred to as a colorimetric object) is the same, depending on a difference in optical system and a difference in wavelength calibration method, or the like, measurement values of the spectral reflectance may be different from each other. For this reason, if different spectrocolorimetric devices are used in parallel for measurement with respect to similar colorimetric objects such as the same products, in some cases, the spectral reflectances obtained for the spectrocolorimetric devices and the color values calculated from the spectral reflectances may be different. In this case, it is difficult to appropriately manage the color of the colorimetric object.

With respect to such a problem, in a first spectrocolorimetric device 1m (refer to FIG. 1) according to an embodiment, a spectral reflectance (also referred to as a first spectral reflectance) acquired by measurement using the first spectrocolorimetric device 1m may be converted into a spectral reflectance (also referred to as a second spectral reflectance) that can be acquired by measurement using a second spectrocolorimetric device 1t (refer to FIG. 2) different from the first spectrocolorimetric device 1m. At this time, the second spectrocolorimetric device 1t is another spectrocolorimetric device (also referred to as a destination-of-conversion spectrocolorimetric device) as a destination-of-conversion of the first spectral reflectance obtained by the first spectrocolorimetric device 1m. In addition, in the embodiment, for example, the first and second spectrocolorimetric devices 1m and 1t may be devices of different models or different devices of the same model.

However, in order to set a rule (also referred to as a conversion rule) for converting the first spectral reflectance into the second spectral reflectance by using the above-described Mathematical Formula (1) in the related art, it is necessary to prepare a large number of calibration samples, and it takes a long time to perform the measurement using a large number of the calibration samples. Furthermore, it is not easy to secure a conversion accuracy (robustness) depending on a method of selecting the calibration sample. For this reason, complicated manipulations or operations are required for setting a conversion rule, and it is not easy to set the conversion rule at a high accuracy.

Therefore, in the embodiment, the deviation between the first spectral reflectance and the second spectral reflectance is treated to be divided into the deviation (appropriately abbreviated to the deviation relating to linearity) relating to linearity of the reflectance and the deviation relating to the spectral sensitivity, and the conversion rule is set. Therefore, it is possible to set the conversion rule by using a small number of calibration samples. Namely, a highly-accurate conversion rule of measurement values between different spectrocolorimetric devices can be easily set.

Herein, a deviation relating to the linearity is, for example, a deviation (also referred to as a first deviation) of the spectral reflectance in the reflectance direction occurring due to a difference in a relationship between an intensity of reflected light actually generated on a colorimetric object for each wavelength and an intensity of reflected light to be measured between the devices. In other words, the deviation relating to the linearity corresponds to a difference (also referred to as a reflectance difference) of the reflectance as a component of the deviation (also referred to as a deviation component) relating to the reflectance for each wavelength between the first spectral reflectance and the second spectral reflectance. In addition, a deviation relating to the spectral sensitivity is, for example, a deviation (also referred to as a second deviation) of spectral reflectance in the wavelength direction as an error (also referred to as a calibration error) occurring due to different wavelength calibration methods between the devices in calibrating the spectral sensitivity.

<(1-2) Schematic Configuration of Spectrocolorimetric Device>

FIG. 1 is a diagram schematically illustrating a configuration example of a first spectrocolorimetric device 1m according to an embodiment. FIG. 2 is a diagram schematically illustrating a configuration example of a second spectrocolorimetric device 1t. Herein, an example where the configuration of 45/0 (45° illumination and vertical reception) recommended by the International Commission on Illumination (CIE) is employed will be described. For example, the configuration of 0/45 (vertical illumination and 45° reception) recommended by the CIE may be employed.

For example, each of the first and second spectrocolorimetric devices 1m and 1t is configured to have a housing 2 and a light source 11, a light-emitting circuit 12, a light-receiving unit 13, a control unit 14, a storage unit 15 and an input/output unit 16 which are enclosed in the housing 2.

The housing 2 is configured to have an opening 2o. Herein, an example is employed where the second spectrocolorimetric device 1t is provided with a transparent member (also referred to as a transparent member) 17t for preventing particles (dust or the like) from intruding into the housing 2 through the opening 2o whereas the first spectrocolorimetric device 1m is not provided with a transparent member. The transparent member 17t has a shape of, for example, a convex lens or a plate, and as a material of the transparent member 17t, for example, colorless transparent glass or acrylic or the like may be employed. The opening 2o passes the light (also referred to as illumination light) emitted from the light source 11 toward the outside of the housing 2, so that a colorimetric object 100 arranged in the vicinity of the opening 2o outside the housing 2 is irradiated with the illumination light. The opening 2o passes the reflected light generated on the surface of the colorimetric object 100 according to the irradiation of the colorimetric object 100 with the illumination light emitted from the light source 11 toward the inside of the housing 2.

The light source 11 emits, for example, white light. As the light source 11 emitting white light, for example, a lamp such as a xenon (Xe) flash lamp may be employed.

The light-emitting circuit 12 is a circuit that allows the light source 11 to emit light under the control of the control unit 14.

The light-receiving unit 13 spectroscopically disperses the reflected light generated on the surface of the colorimetric object 100 according to the irradiation of the colorimetric object 100 with the illumination light emitted from the light source 11 and measures the spectroscopic spectrum relating to the intensity of the reflected light. FIG. 3 is a diagram schematically illustrating a configuration example of the light-receiving unit 13. As illustrated in FIG. 3, the light-receiving unit 13 is configured to include, for example, a slit plate 131, a spectroscopic unit 132, and a sensor unit 133.

The slit plate 131 is a plate-shaped member having a slit-shaped opening (also referred to as a slit portion) 131s for allowing a portion of light (also referred to as incident light) L0 of the reflected light from the colorimetric object 100 to be incident into the light-receiving unit 13.

The spectroscopic unit 132 is a member that spectroscopically disperses the incident light L0 incident from the slit portion 131s according to the wavelength and is configured with, for example, a diffraction grating or the like. In addition, in FIG. 3, among the light beams of a plurality of wavelengths obtained by spectroscopically dispersing the incident light L0 by the spectroscopic unit 132, the outer edge of the light flux of red light (also referred to as red light) Lr1 is drawn by a solid arrow, and the outer edge of the light flux of blue light (also called blue light) Lb1 is drawn by a one-dot dashed line.

The sensor unit 133 is a unit that measures the intensity of light spectroscopically dispersed by the spectroscopic unit 132 for each wavelength and is configured to include, for example, a line sensor (also referred to as a linear array sensor) where a plurality of light-receiving elements arranged in a line.

In the light-receiving unit 13 having such a configuration, the incident light L0 incident from the slit portion 131s is spectroscopically dispersed by the spectroscopic unit 132 and then emitted to the sensor unit 133, so that the intensity of light for each wavelength of the incident light L0 is measured by the sensor unit 133.

The control unit 14 is an electric circuit that performs various types of information processing and is configured to mainly include a processor P0 and a memory M0. In the control unit 14, the processor P0 reads and executes a program (a program P1 in the first spectrocolorimetric device 1m and a program P2 in the second spectrocolorimetric device 1t) stored in the storage unit 15, so that functions of controlling each unit and performing various operations in the first spectrocolorimetric device 1m (or the second spectrocolorimetric device 1t) are realized. The memory M0 is, for example, a volatile storage medium such as a RAM and temporarily stores data generated by various operations in the control unit 14.

The storage unit 15 is configured with, for example, a nonvolatile storage medium and stores programs (the program P1 in the first spectrocolorimetric device 1m and the program P2 in the second spectrocolorimetric device 1t) and various types of information and the like used for various calculations in the control unit 14. In addition, in the first and second spectrocolorimetric devices 1m and 1t, since the programs P1 and P2 executed by the control unit 14 are different, the various functions realized by the control unit 14 are different.

The input/output unit 16 includes, for example, an operation unit, a display unit, and the like. The input/output unit 16 has, for example, a function of inputting signals according to operations of the operation unit by a user and a function of visibly outputting various types of information and the like as calculation results in the control unit 14 on the display unit.

<(1-3) Deviation of Spectral Reflectance Between Devices>

Figure 4:
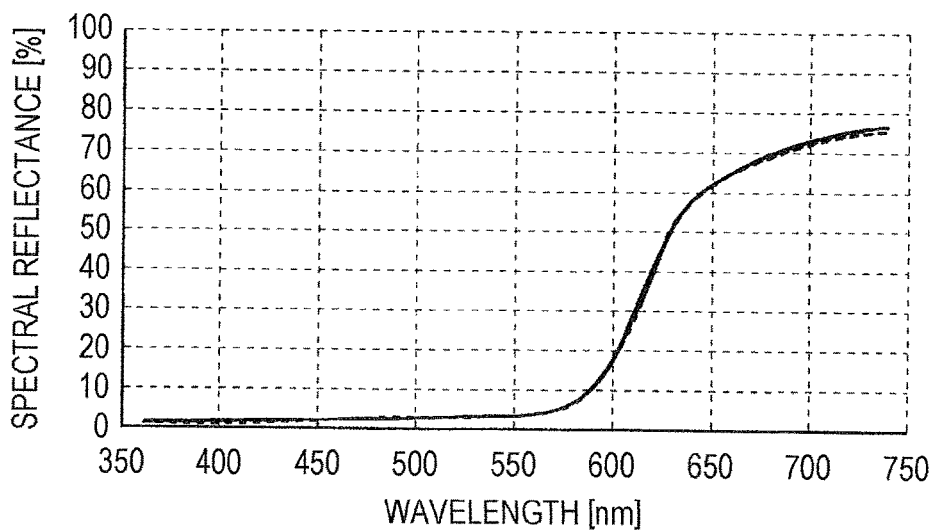
FIG. 4 is a diagram exemplifying first and second spectral reflectances relating to a red colorimetric object.
Figure 5:
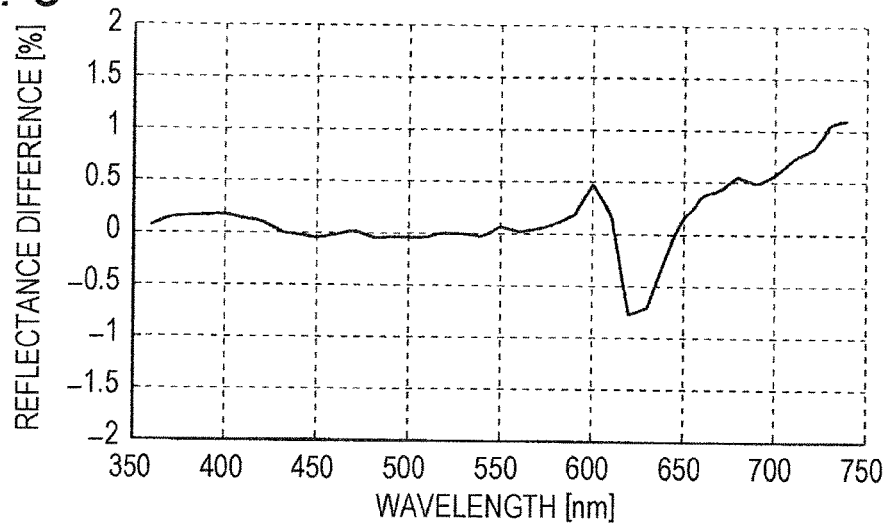
FIG. 5 is a diagram exemplifying a difference between first and second spectral reflectances.

FIG. 4 is a graph exemplifying the spectral reflectance (first spectral reflectance) $R_m(\lambda)$ measured by the first spectrocolorimetric device 1m and the spectral reflectance (second spectral reflectance) $R_t(\lambda)$ measured by the second spectrocolorimetric device 1t for the same red tile as the colorimetric object 100. In addition, in FIG. 4, the horizontal axis indicates the wavelength λ of the light, and the vertical axis indicates the spectral reflectance R(λ) on the surface of the colorimetric object 100. FIG. 5 is a graph exemplifying the difference $\Delta R(\lambda)$ (=$R_m(\lambda)$–$R_t(\lambda)$) between the first spectral reflectance $R_m(\lambda)$ obtained by the first spectrocolorimetric device 1m and the second spectral reflectance $R_t(\lambda)$ obtained by the second spectrocolorimetric device 1t. In FIG. 5, the horizontal axis indicates the wavelength λ, the vertical axis indicates the reflectance difference ΔR, and the relationship between the wavelength λ and the reflectance difference ΔR is drawn by a solid line.

As illustrated in FIG. 5, even when the same red tile is measured, the measurement values of the spectral reflectance are different between the devices. The deviation in spectral reflectance between the devices is classified into the first deviation relating to the linearity and the second deviation relating to the spectral sensitivity as described above. Herein, the first deviation relating to the linearity and the second deviation relating to the spectral sensitivity will be specifically described.

<(1-3-1) Deviation Relating to Linearity (First Deviation)>

Figure 6:
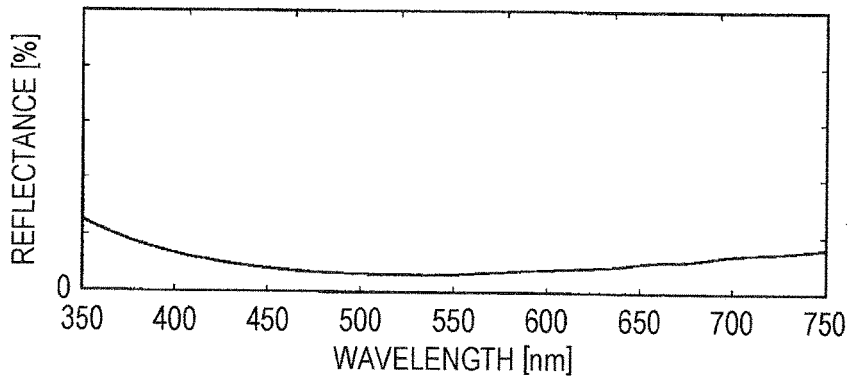
FIG. 6 is a diagram exemplifying a spectral reflectance of a transparent member.

FIG. 6 is a diagram illustrating an example of a spectral reflectance of the transparent member 17t. The transparent member 17t provided in the second spectrocolorimetric device 1t exhibits a spectral reflectance as illustrated in FIG. 6, for example, by antireflection coating applied to the surface.

As illustrated in FIG. 2, in the second spectrocolorimetric device 1t, for example, after the irradiation light emitted from the light source 11 is reflected on the surface of the colorimetric object 100, the light passing through the transparent member 17t and further the light that is retroreflected, namely, sequentially reflected on the surface of the transparent member 17t and the surface of the colorimetric object 100 and then passes through the transparent member 17t is received by the light-receiving unit 13. On the other hand, as illustrated in FIG. 1, in the first spectrocolorimetric device 1m, for example, after the irradiation light emitted from the light source 11 is reflected on the surface of the colorimetric object 100, the light is simply received by the light-receiving unit 13. As described above, even when the colorimetric object 100 is the same between the first and second spectrocolorimetric devices 1m and 1t, since the paths of light from the light source 11 to the light-receiving unit 13 are different, the acquired spectral reflectances may be different.

Herein, for example, in the first and second spectrocolorimetric devices 1m and 1t, white calibration using a white calibration plate having a reflectance of about 100% and black calibration using a black calibration plate having a reflectance of about 0% are assumed to be performed. In this case, if the colorimetric object 100 is white, the spectroscopic spectrum priced for the white calibration plate can be measured by the first and second spectrocolorimetric devices 1m and 1t, respectively. In addition, if the colorimetric object 100 is black, spectroscopic spectrum priced for the black calibration plate can be measured by the first and second spectrocolorimetric devices 1m and 1t, respectively. Namely, if the colorimetric object 100 is white or black, the same spectral reflectance can be acquired between the first and second spectrocolorimetric devices 1m and 1t, respectively. On the other hand, in the case where the colorimetric object 100 has an approximately intermediate reflectance (for example, about 50%) between white and black, in the spectroscopic spectra measured by the first and second spectrocolorimetric devices 1m and 1t, respectively, the largest deviation caused by retroreflection may occur.

In addition, as illustrated in FIG. 6, the spectral reflectance of the transparent member 17t is not constant with respect to the wavelength. For this reason, for example, with respect to a wavelength at which the reflectance of the transparent member 17t is 0%, no retroreflection occurs between the transparent member 17t and the colorimetric object 100. On the other hand, as for the wavelength of the transparent member 17t having a relatively high reflectance, the deviation of the acquired spectral reflectance greatly differs between the devices due to the retroreflection between the transparent member 17t and the colorimetric object 100. As described above, the first deviation relating to the linearity caused by the retroreflection among the acquired spectral reflectances differs depending on the wavelength of light and the reflectance of the colorimetric object 100.

In addition, in the examples illustrated in FIGS. 4 and 5, in the wavelength range in the vicinity of 650 to 740 nm, the change in reflectance with respect to the change in wavelength is relatively small. Therefore, among the deviations of the spectral reflectance acquired between the devices illustrated in FIGS. 4 and 5, the deviation in spectral reflectance at a wavelength in the vicinity of 650 to 740 nm corresponds to the first deviation relating to the linearity due to retroreflection.

<(1-3-2) Deviation Relating to Spectral Sensitivity (Second Deviation)>

Figure 7:
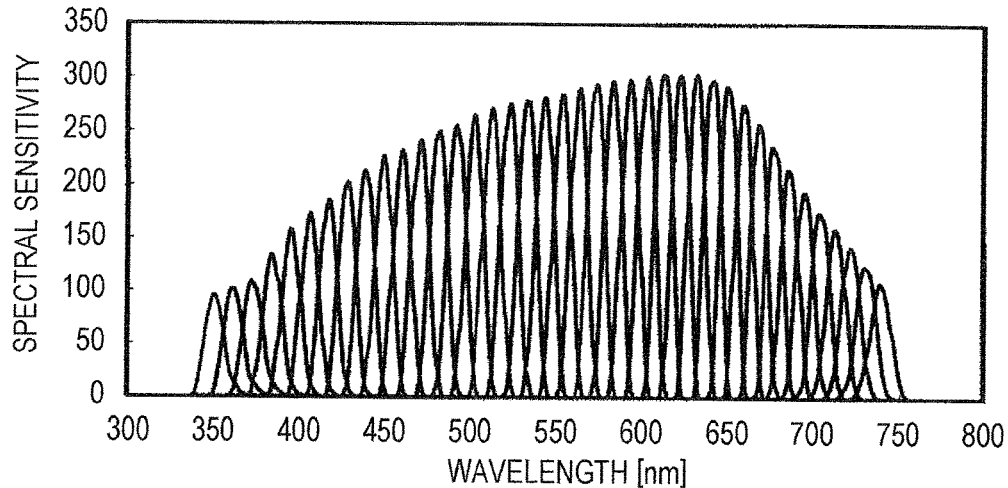
FIG. 7 is a diagram exemplifying a spectral sensitivity of each light-receiving element of a light-receiving unit.

FIG. 7 is a diagram illustrating a spectral sensitivity of each light-receiving element constituting the sensor unit 133 of the light-receiving unit 13. In the first and second spectrocolorimetric devices 1m and 1t, the respective light-receiving units 13 have different spectral sensitivities. For this reason, for example, a function (for example, a function that defines a center wavelength, a full width at half maximum, or the like) that defines the spectral sensitivity of each light-receiving element is calibrated by different wavelength calibration methods for different devices, so that the correction according to the spectral sensitivity of each light-receiving element can be performed. Herein, as a wavelength calibration method, for example, there are a number of calibration methods such as a calibration method using a monochromator and a calibration method using a bright-line light source, or the like as described below, and thus, different wavelength calibration methods for different models may be employed.

In the calibration method using a monochromator, for example, monochromatic light emitted by a monochromator is incident on a spectrocolorimetric device while the wavelength of the monochromatic light being shifted in time, and thus, the wavelength is calibrated so that the spectroscopic spectrum of monochromatic light of each wavelength coincides with the spectroscopic spectrum detected by the spectrocolorimetric device. In addition, as the pitch at which the wavelength of the monochromatic light is shifted, for example, 1 nm or the like may be employed. However, in the calibration method using the monochromator, since monochromatic light of each wavelength tends to have a weak light amount, the exposure time for receiving monochromatic light in the spectrocolorimetric device can be increased. Furthermore, the number of scanning wavelength points of monochromatic light of a plurality of wavelengths is very large, and thus, it takes a long time to calibrate the wavelength.

In the calibration method using the bright-line light beams, for example, light beams of a plurality of specific wavelengths emitted from the bright-line light source are input to the spectrocolorimetric device, and the wavelength is calibrated so that spectroscopic spectrum relating to the intensity of the light beam of each of the specific wavelengths coincides with the spectroscopic spectrum detected by the spectrocolorimetric device. In addition, as the bright-line light source, for example, a mercury lamp, a mercury cadmium lamp, or the like may be employed. With respect to the calibration method using the bright-line light beams, for example, light beams of a plurality of specific wavelengths are simultaneously emitted from the bright-line light source, and light amounts of the light beams of the respective specific wavelengths are also high, so that the time required for calibration can be shortened. However, in the calibration method using the bright-line light beams, the calibration accuracy is low for wavelengths deviated from a plurality of specific wavelengths.

Herein, if the wavelength calibration methods are different between the first and second spectrocolorimetric devices 1m and 1t, for example, the accuracies of the calibration relating to the center wavelength and the full width at half maximum of the spectral sensitivities of the light-receiving elements between the first and second spectrocolorimetric devices 1m and 1t are different from each other. In addition, if the wavelength calibration methods are different between the first and second spectrocolorimetric devices 1m and 1t, even though the colorimetric object 100 is the same, the spectroscopic spectra of the reflected light acquired by the spectrocolorimetric devices 1m and 1t are different from each other. Specifically, between the first and second spectrocolorimetric devices 1m and 1t, the spectral reflectance acquired according to the difference in the wavelength calibration method may be deviated in the wavelength direction, or the waveform of the spectral reflectance may be corrupted so that a difference in the spectral reflectance occurs as a measurement result.

In addition, in the example illustrated in FIGS. 4 and 5, in the wavelength range in the vicinity of 550 to 650 nm, the change in reflectance with respect to the change in wavelength is large. Therefore, among the deviations of the spectral reflectances acquired between the devices illustrated in FIGS. 4 and 5, the deviation in spectral reflectance at a wavelength in the vicinity of 550 to 650 nm corresponds to the second deviation relating to the spectral sensitivity.

<(1-4) Correction of Deviation in Spectral Reflectance Between Devices>

For example, if the first and second spectrocolorimetric devices 1m and 1t are products of the same manufacturer and the first spectrocolorimetric device 1m is a successor of the second spectrocolorimetric device 1t, a user may expect that the measurement values similar to those of the second spectrocolorimetric device 1t can be obtained for the same colorimetric object 100 by the first spectrocolorimetric device 1m. In order to respond to such expectation, in the embodiment, the deviation in spectral reflectance between the devices is considered, and the spectral reflectance acquired by the first spectrocolorimetric device 1m is converted to the spectral reflectance that can be acquired the second spectrocolorimetric device 1t.

As described above, the deviation in spectral reflectance between the devices is a mixture of the first deviation relating to the linearity and the second deviation relating to the spectral sensitivity. Therefore, if the first deviation relating to the linearity and the second deviation relating to the spectral sensitivity are not distinguished from each other, it is necessary to employ such a method as to set a conversion rule for converting the first spectral reflectance into the second spectral reflectance by using, for example, the above-described Mathematical Formula (1) in the related art. However, Mathematical Formula (1) is a very complicated formula, and the coefficients A(i), B(i), C(i), D(i), and E(i) need to be obtained for each wavelength λ(i) of each light receiving element. Therefore, it is necessary to prepare a large number of calibration samples, and it takes a long time to perform the measurement using a large number of the calibration samples. In addition, the robustness of the coefficients A(i), B(i), C(i), D(i), and E(i) to be obtained may be deteriorated depending on the characteristics of the calibration sample.

Therefore, in the embodiment, the deviation between the first spectral reflectance acquired by the first spectrocolorimetric device 1m and the second spectral reflectance acquired by the second spectrocolorimetric device 1t is treated to be divided into the first deviation relating to the linearity and the second deviation relating to the spectral sensitivity, and the conversion rule is set. As a result, by using a small number of calibration samples, a highly-accurate conversion rule of measurement values between different spectrocolorimetric devices can be easily set.

In addition, for example, if both the first and second spectrocolorimetric devices 1m and 1t are products of the same manufacturer, information relating to various types of calibration is known by the manufacturer. Therefore, in the first spectrocolorimetric device 1m, for example, by using information on various types of known calibration, a highly-accurate conversion rule of measurement values between different spectrocolorimetric devices can be easily set.

Figure 8:
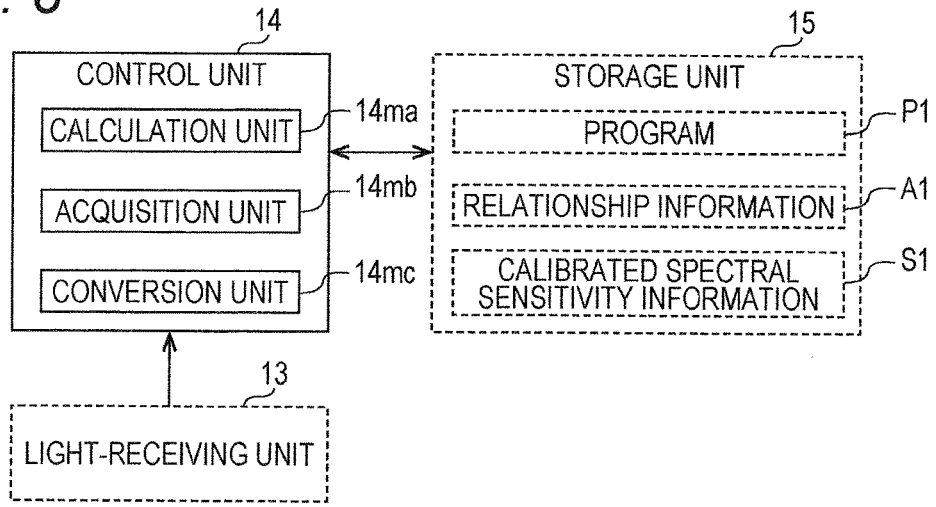
FIG. 8 is a diagram exemplifying a functional configuration realized by a control unit of a first spectrocolorimetric device.

FIG. 8 is a diagram exemplifying a functional configuration realized by the control unit 14 of the first spectrocolorimetric device 1m in order to correct the deviation in spectral reflectance between the devices.

As illustrated in FIG. 8, the control unit 14 of the first spectrocolorimetric device 1m is configured to include a calculation unit 14ma, an acquisition unit 14mb, and a conversion unit 14mc, as a functional configuration realized by executing the program P1 by the processor P0.

The calculation unit 14ma calculates the spectral reflectance (first spectral reflectance) of the colorimetric object 100 from the spectroscopic spectrum relating to the reflected light from the colorimetric object 100 measured by the light-receiving unit 13 of the first spectrocolorimetric device 1m. In the calculation unit 14ma, for example, the first spectral reflectance can be calculated on the basis of the preset spectroscopic spectrum of the light emitted from the light source 11 and the spectroscopic spectrum relating to the measured reflected light.

The acquisition unit 14mb acquires the reflectance difference as the deviation component relating to the reflectance for each wavelength of the light between the first spectral reflectance and the second spectral reflectance on the basis of the first spectral reflectance calculated by the calculation unit 14ma and relationship information A1 stored in the storage unit 15. Herein, the relationship information A1 is information indicating the relationship between the reflectance and the reflectance difference for each wavelength of light and is information defining a conversion rule (also referred to as a first conversion rule) for correcting the first deviation relating to the linearity in order to convert the first spectral reflectance $R_m(\lambda)$ into the second spectral reflectance $R_t(\lambda)$.

Herein, the first spectral reflectance $R_m(\lambda)$ is obtained by actual measurement using the first spectrocolorimetric device 1m. The second spectral reflectance $R_t(\lambda)$ is an estimated value (also referred to as a second estimated spectral reflectance) that is estimated to be obtained by measurement using the second spectrocolorimetric device 1t as a destination-of-conversion spectrocolorimetric device different from the first spectrocolorimetric device 1m. For example, the reflectance difference for each wavelength can be acquired, for example, on the basis of the difference between the spectral reflectance obtained by measurement using the first spectrocolorimetric device 1m and the spectral reflectance obtained by measurement using the second spectrocolorimetric device 1t for the same calibration sample in advance. Therefore, for example, for each wavelength, the relationship between the reflectance and the reflectance difference corresponding to the first spectral reflectance acquired by measurement using the first spectrocolorimetric device 1m can be acquired.

The conversion unit 14mc adds or subtracts the reflectance difference for each wavelength acquired by the acquisition unit 14mb to or from the first spectral reflectance calculated by the calculation unit 14ma to convert the first spectral reflectance into the second spectral reflectance. Herein, for example, if the reflectance difference defined by the relationship information A1 represents the magnitude of the first spectral reflectance with respect to the second spectral reflectance as a reference as a positive/negative numerical value, the conversion unit 14mc may substrate the reflectance difference for each wavelength acquired by the acquisition unit 14mb from the first spectral reflectance calculated by the calculation unit 14ma. Conversely, if the reflectance difference represents the magnitude of the second spectral reflectance with respect to the first spectral reflectance as a reference, the conversion unit may add the reflectance difference to the first spectral reflectance.

In the case where such a configuration is employed, in addition to the second deviation relating to the spectral sensitivity, for the first deviation relating to the linearity, the relationship between the reflectance for each wavelength and the reflectance difference as a deviation component relating to the reflectance is set. Therefore, in order to correct the first deviation relating to the linearity, a highly-accurate conversion rule of measurement value between the different first and second spectrocolorimetric devices 1m and 1t can be easily set.

In addition, the conversion unit 14mc can calculate the estimated value (second estimated spectral reflectance) $R^*_t(\lambda^*_{G\_t}(k))$ of the spectral reflectance that is estimated to be acquired in the second spectrocolorimetric device 1t from the spectroscopic spectrum by using the calibrated spectral sensitivity (also referred to as the calibrated spectral sensitivity) of the second spectrocolorimetric device 1t different from the first spectrocolorimetric device 1m and the spectroscopic spectrum measured by the light-receiving unit 13 of the first spectrocolorimetric device 1m. Herein, k is a natural number of 1 to K0 for defining the wavelength and may be, for example, a numerical value that defines the order of the first to K0-th light-receiving elements in the sensor unit 133.

In the case where such a configuration is employed, in addition to the first deviation relating to linearity, information (also referred to as calibrated spectral sensitivity information) S1 indicating the calibrated spectral sensitivity with respect to the deviation relating to the spectral sensitivity is set. Namely, the calibrated spectral sensitivity information S1 is information defining a conversion rule (also referred to as a second conversion rule) for correcting the second deviation relating to the spectral sensitivity to convert the first spectral reflectance $R_m(\lambda)$ to the second spectral reflectance $R_t(\lambda)$. As a result, in order to correct the second deviation relating to the spectral sensitivity, a highly-accurate conversion rule of the measurement value between the different first and second spectrocolorimetric devices 1m and 1t can be easily set.

In addition, as described above, the conversion unit 14mc adds or subtracts the reflectance difference for each wavelength acquired by the acquisition unit 14mb to or from the first spectral reflectance $R_m(\lambda)$, and the second spectral reflectance $R_t(\lambda)$ that can be acquired by the second spectrocolorimetric device 1t from the spectroscopic spectrum may be calculated by using the calibrated spectral sensitivity information S1 of the second spectrocolorimetric device 1t and the spectroscopic spectrum measured by the first spectrocolorimetric device 1m. At this time, for example, the conversion unit 14mc adds or subtracts the reflectance difference for each wavelength acquired by the acquisition unit 14mb to or from the spectral reflectance acquired by using the spectroscopic spectrum and the calibrated spectral sensitivity, so that the second spectral reflectance that can be acquired by the second spectrocolorimetric device 1t is calculated.

In the case where such a configuration is employed, the difference between the first spectral reflectance $R_m(\lambda)$ acquired by the first spectrocolorimetric device 1m and the second spectral reflectance $R_t(\lambda)$ acquired by the second spectrocolorimetric device $1t$ is divided into the first deviation relating to the linearity and the second deviation relating to the spectral sensitivity, and thus, the conversion rule is set. Thus, in order to correct the first deviation relating to the linearity and the second deviation relating to the spectral sensitivity, it is possible to set the conversion rule by using a relatively small number of calibration samples. Namely, a highly-accurate conversion rule of measurement values between the different first and second spectrocolorimetric devices $1m$ and $1t$ can be easily set.

Figure 9:
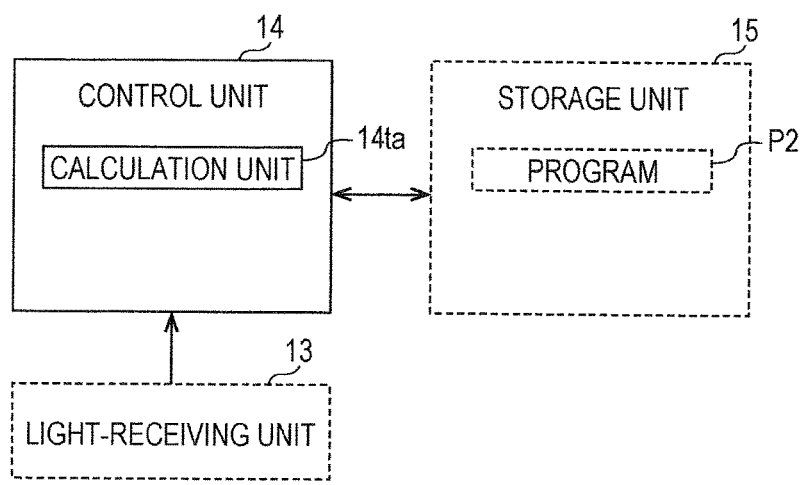
FIG. 9 is a diagram exemplifying a functional configuration realized by a control unit of a second spectrocolorimetric device.

FIG. 9 is a diagram exemplifying a functional configuration realized by the control unit 14 of the second spectrocolorimetric device $1t$. As illustrated in FIG. 9, the control unit 14 of the second spectrocolorimetric device $1t$ has a calculation unit 14$ta$ as a functional configuration realized by executing the program P2 by the processor P0. The calculation unit 14$ta$ calculates the spectral reflectance (the second spectral reflectance) $R_t(\lambda)$ relating to the colorimetric object 100 from the spectroscopic spectrum relating to the reflected light from the colorimetric object 100 measured by the light-receiving unit 13 of the second spectrocolorimetric device $1t$. In the calculation unit 14$ta$, for example, the second spectral reflectance can be calculated on the basis of the preset spectroscopic spectrum of the light emitted from the light source 11 and the spectroscopic spectrum relating to the measured reflected light.

Hereinafter, the correction of the first deviation relating to the linearity between the devices and the correction of the second deviation relating to the spectral sensitivity will be sequentially described.

<(1-4-1) Correction of Deviation (First Deviation) Relating to Linearity Between Devices>

For example, in the case where the colorimetric object 100 has a spectral reflectance so that the reflectance is substantially constant irrespective of the wavelength of light, an error (a second deviation relating to the spectral sensitivity) of the spectral reflectance due to the deviation of the spectral sensitivity between the devices is hardly generated. Specifically, for example, if the reflectance is substantially constant irrespective of the wavelength in the spectral reflectance, even though the center wavelength and the full width at half maximum that define the spectral sensitivity in each light-receiving element are deviated between the devices, the spectroscopic spectrum relating to the intensity of the light received in each of the light-receiving elements is hardly changed. As described above, as the colorimetric object 100 having a spectral reflectance, of which reflectance is substantially constant irrespective of the wavelength of light, for example, a calibration sample of which reflectance is included within a width of the predetermined value range in the entire to-be-measured wavelength range may be exemplified.

Herein, as the to-be-measured wavelength range, for example, a wavelength range of about 360 to 740 nm which is a wavelength range of visible light may be employed. As the predetermined value range, for example, a very narrow preset value range may be employed. As the colorimetric object 100 satisfying such a condition, for example, an achromatic sample may be exemplified.

Figure 10:
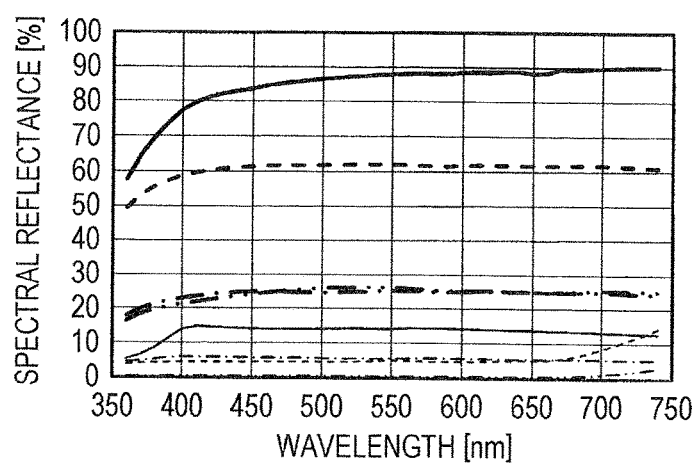
FIG. 10 is a diagram exemplifying a spectral reflectance acquired for an achromatic colorimetric object.

FIG. 10 is a diagram exemplifying a spectral reflectance acquired for the colorimetric object 100 of an achromatic color. In FIG. 10, for achromatic samples with a plurality of types of density ranging from white to black, examples of the first and second spectral reflectances $R_m(\lambda)$ and $R_t(\lambda)$ acquired by the first and second spectrocolorimetric devices $1m$ and $1t$, respectively, are illustrated by curves. Specifically, the first and second spectral reflectances $R_m(\lambda)$ and $R_t(\lambda)$ are illustrated in a graph in which the horizontal axis is the wavelength $\lambda$ and the vertical axis is the reflectance R.

Figure 11:
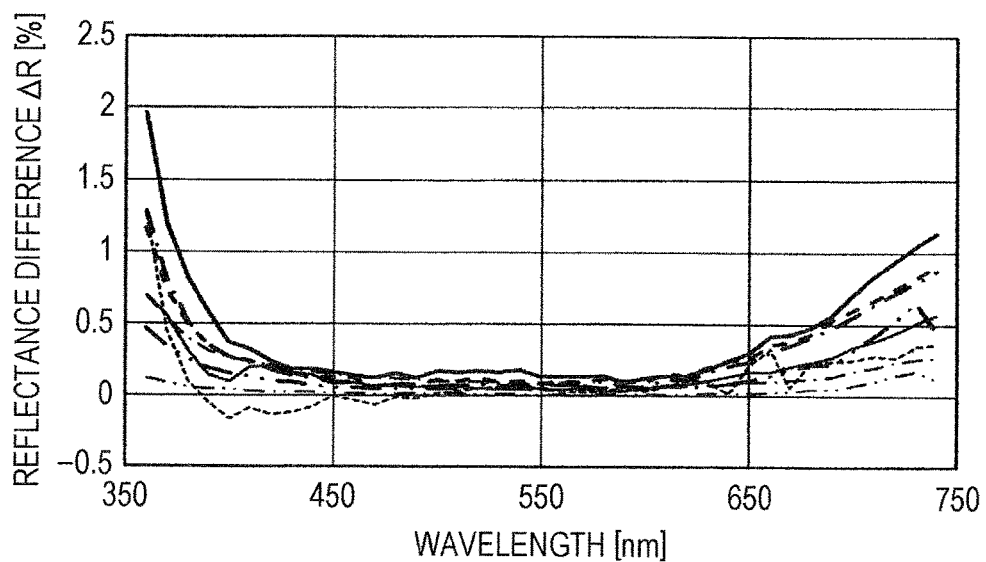
FIG. 11 is a diagram exemplifying a difference between spectral reflectances acquired for the same achromatic colorimetric object between devices.

FIG. 11 is a diagram exemplifying a difference of the spectral reflectance between the devices acquired for the same achromatic colorimetric object 100. In FIG. 11, for achromatic samples with a plurality of types of density ranging from white to black, a difference $\Delta R(\lambda)$ ($=R_m(\lambda)-R_t(\lambda)$) between the first spectral reflectance $R_m(\lambda)$ acquired by the first spectrocolorimetric device $1m$ and the second spectral reflectance $R_t(\lambda)$ acquired by the second spectrocolorimetric device $1t$ is illustrated.

In FIGS. 10 and 11, in the wavelength range of 360 to 400 nm and the wavelength range of 650 to 740 nm where the reflectance of the transparent member 17$t$ is high, between the first and second spectrocolorimetric devices $1m$ and $1t$, a state that a deviation in spectral reflectance between the devices occurs is illustrated. Herein, with respect to the wavelength range excluding the wavelength range where the spectral reflectance of the colorimetric object 100 is changing, the difference (reflectance difference) $\Delta R(\lambda)$ between the first spectral reflectance $R_m(\lambda)$ acquired by the first spectrocolorimetric device $1m$ and the second spectral reflectance $R_t(\lambda)$ acquired by the second spectrocolorimetric device $1t$ corresponds to the first deviation relating to the linearity.

As described above, by using the colorimetric object 100 of which spectral reflectance is substantially constant as a calibration sample, the first deviation relating to the linearity in which the influence of the second deviation relating to the spectral sensitivity among the deviations in spectral reflectance acquired between the devices is eliminated can be detected. As a result, a plurality of calibration samples for obtaining the relationship between the reflectance for each wavelength and the reflectance difference as a deviation component relating to the reflectance can be easily prepared. Namely, the relationship between the reflectance for each wavelength and the reflectance difference as a deviation component relating to the reflectance can be easily obtained.

Herein, the setting of the relationship information A1 indicating the relationship between the reflectance and the reflectance difference for each wavelength will be specifically described.

Figure 12:
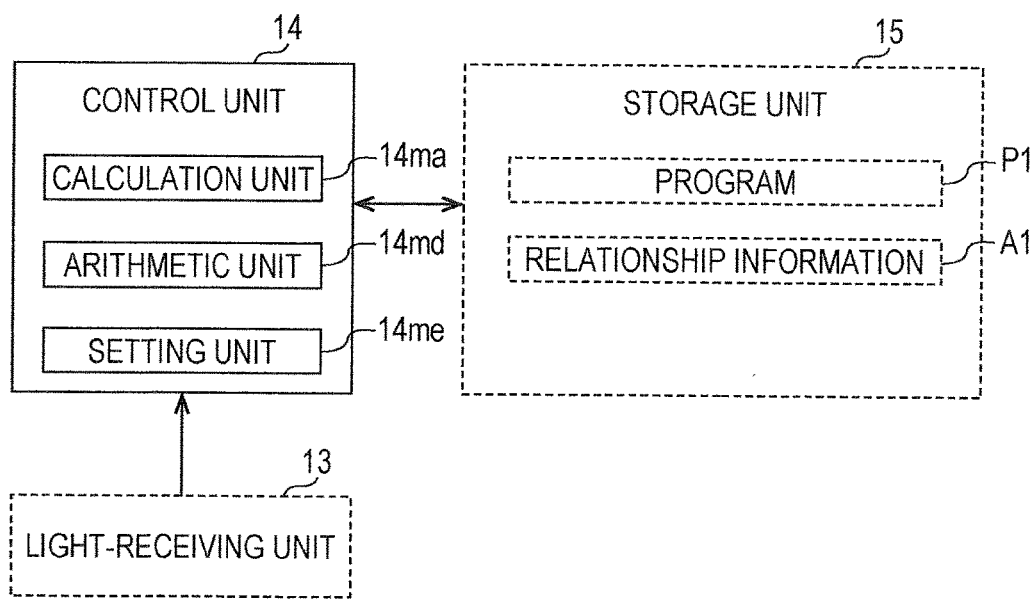
FIG. 12 is a diagram exemplifying a functional configuration realized by a control unit of a first spectrocolorimetric device.
Figure 13:
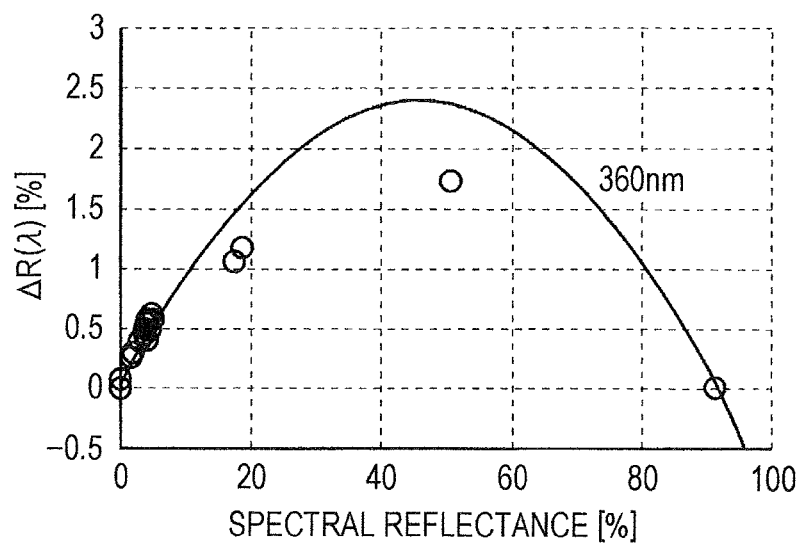
FIG. 13 is a diagram illustrating a relationship between a spectral reflectance and a spectral reflectance difference.
Figure 14:
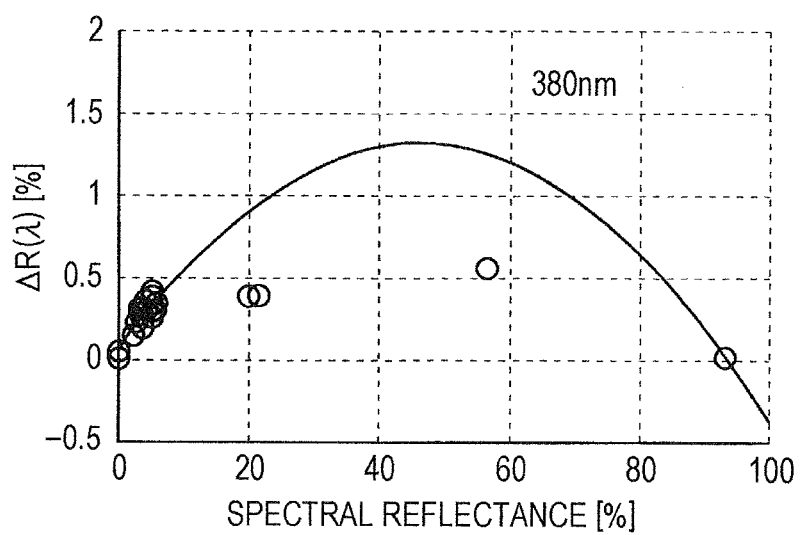
FIG. 14 is a diagram illustrating a relationship between a spectral reflectance and a spectral reflectance difference.
Figure 15:
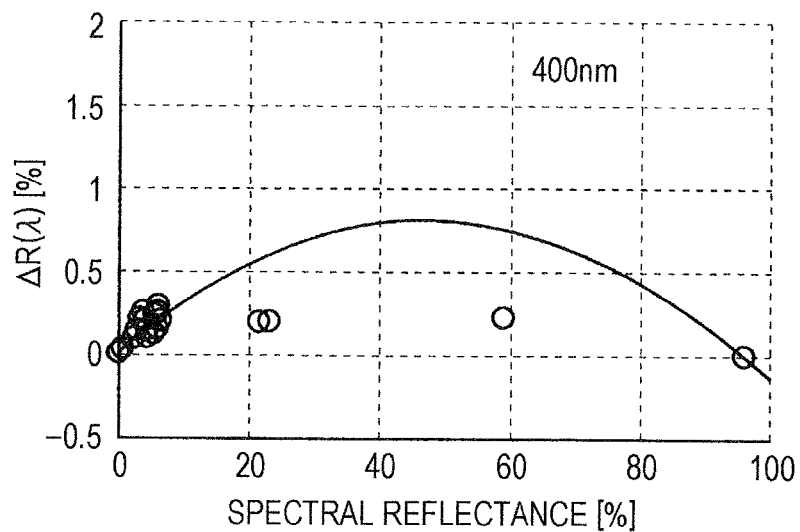
FIG. 15 is a diagram illustrating a relationship between a spectral reflectance and a spectral reflectance difference.
Figure 16:
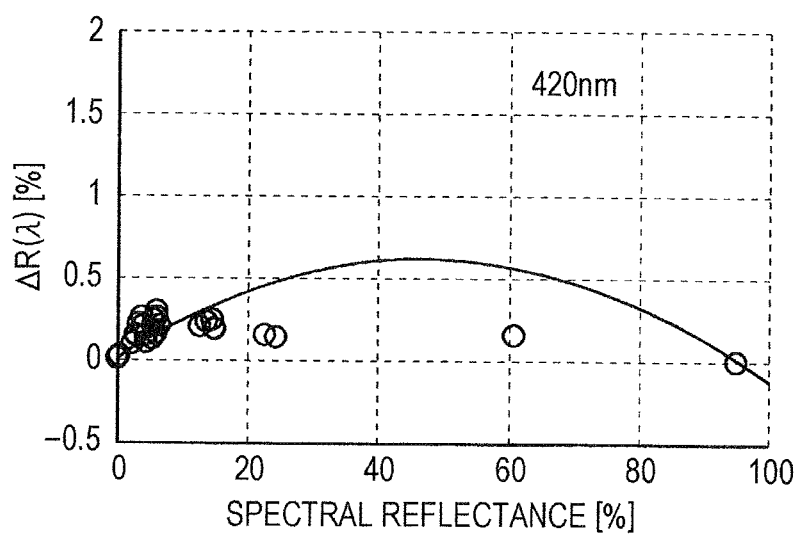
FIG. 16 is a diagram illustrating a relationship between a spectral reflectance and a spectral reflectance difference.
Figure 17:
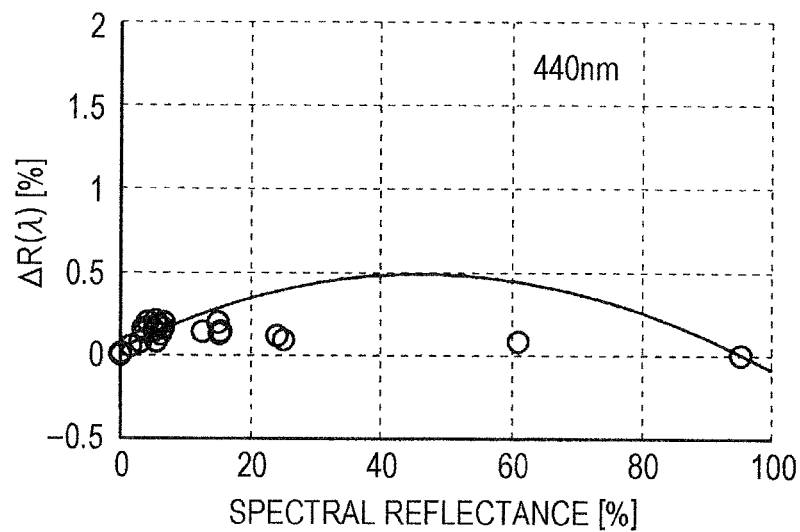
FIG. 17 is a diagram illustrating a relationship between a spectral reflectance and a spectral reflectance difference.
Figure 18:
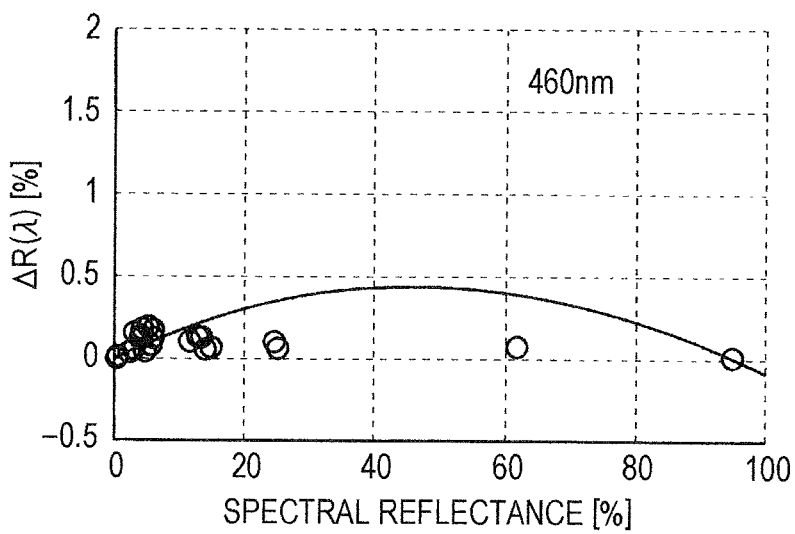
FIG. 18 is a diagram illustrating a relationship between a spectral reflectance and a spectral reflectance difference.
Figure 19:
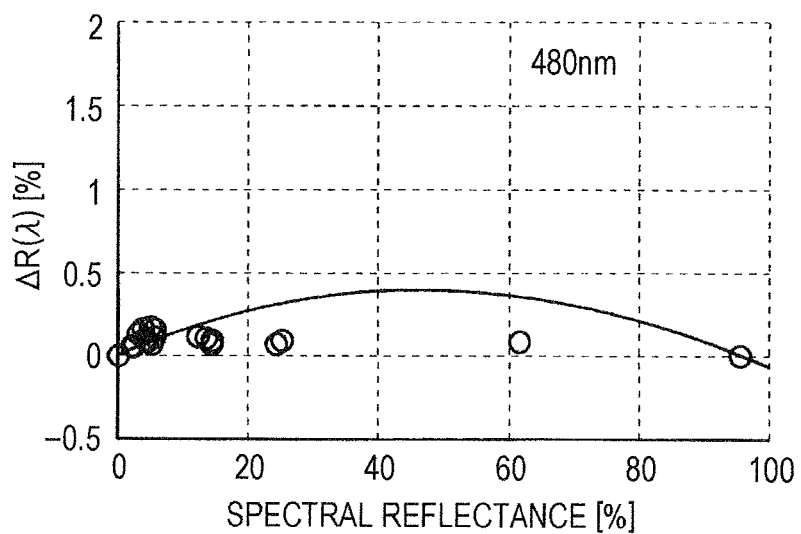
FIG. 19 is a diagram illustrating a relationship between a spectral reflectance and a spectral reflectance difference.
Figure 20:
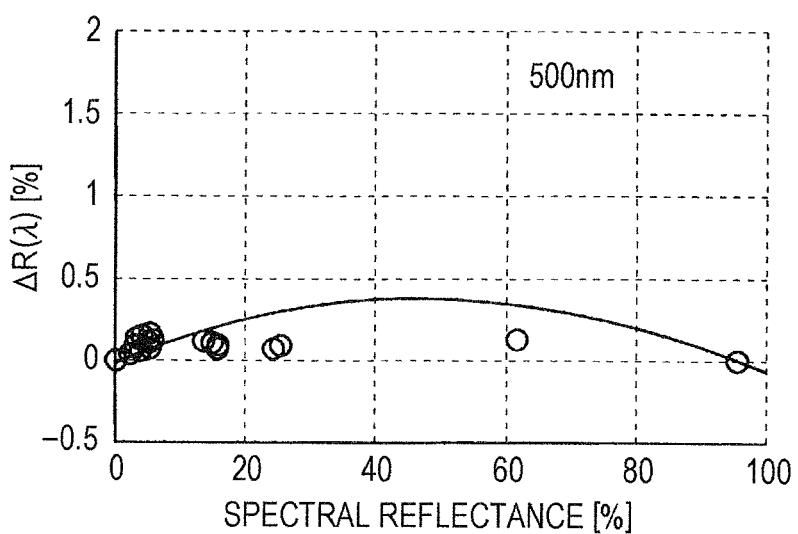
FIG. 20 is a diagram illustrating a relationship between a spectral reflectance and a spectral reflectance difference.
Figure 21:
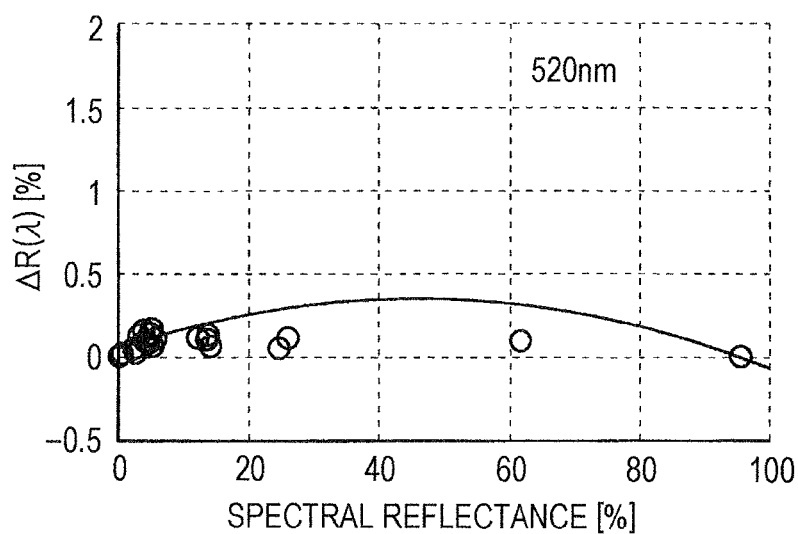
FIG. 21 is a diagram illustrating a relationship between a spectral reflectance and a spectral reflectance difference.
Figure 22:
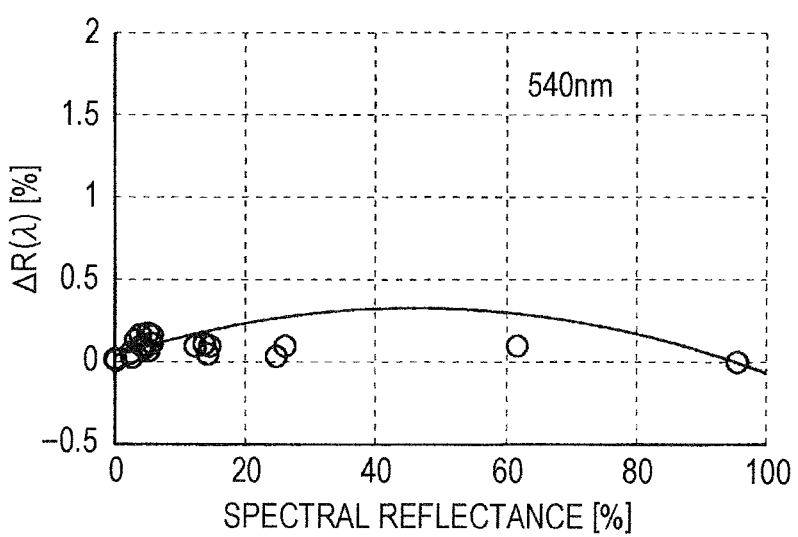
FIG. 22 is a diagram illustrating a relationship between a spectral reflectance and a spectral reflectance difference.
Figure 23:
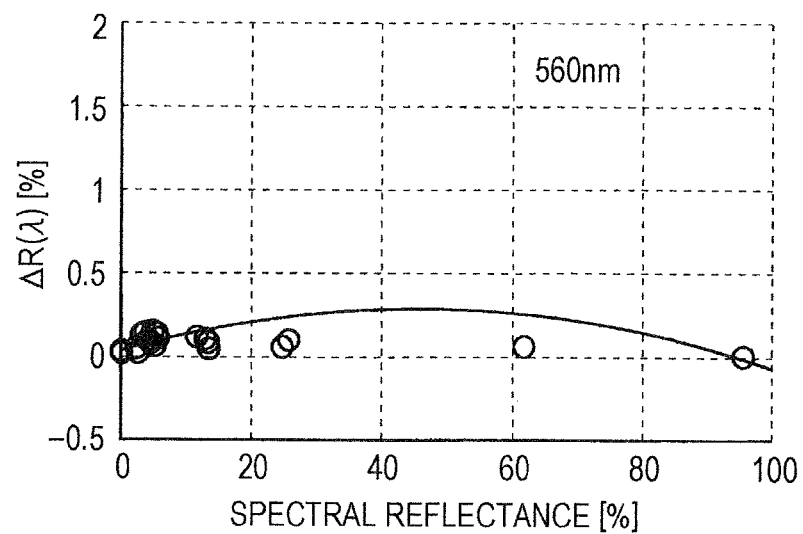
FIG. 23 is a diagram illustrating a relationship between a spectral reflectance and a spectral reflectance difference.
Figure 24:
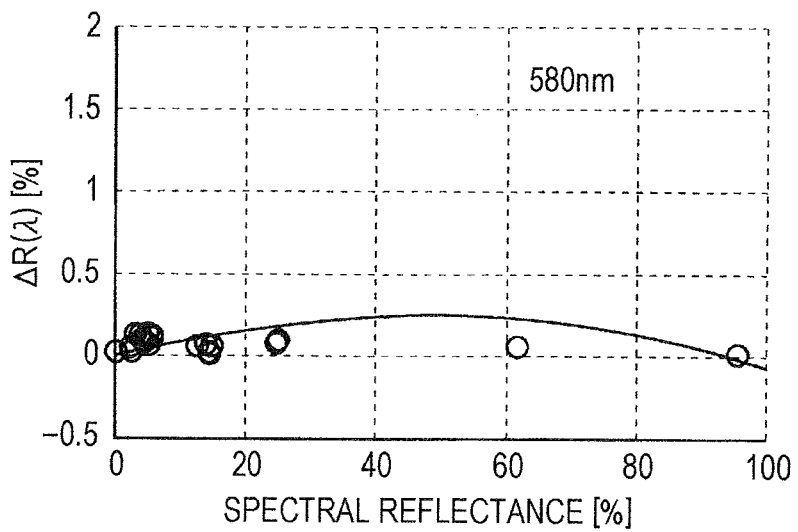
FIG. 24 is a diagram illustrating a relationship between a spectral reflectance and a spectral reflectance difference.
Figure 25:
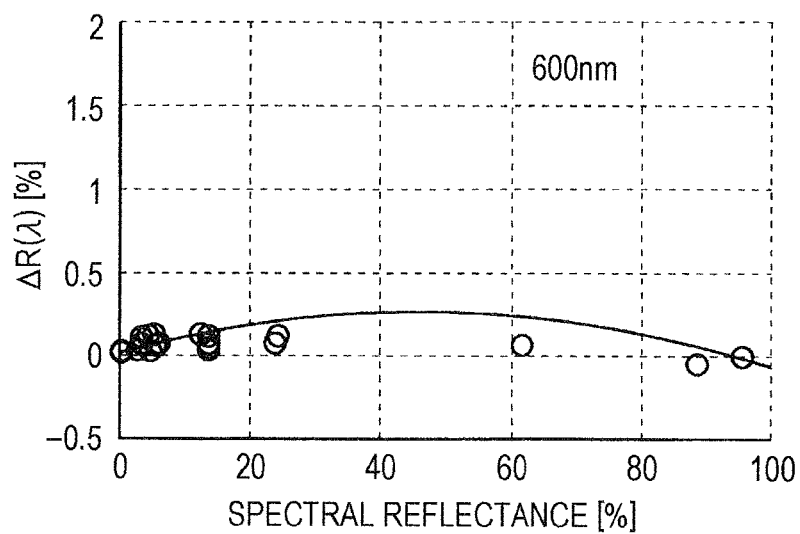
FIG. 25 is a diagram illustrating a relationship between a spectral reflectance and a spectral reflectance difference.
Figure 26:
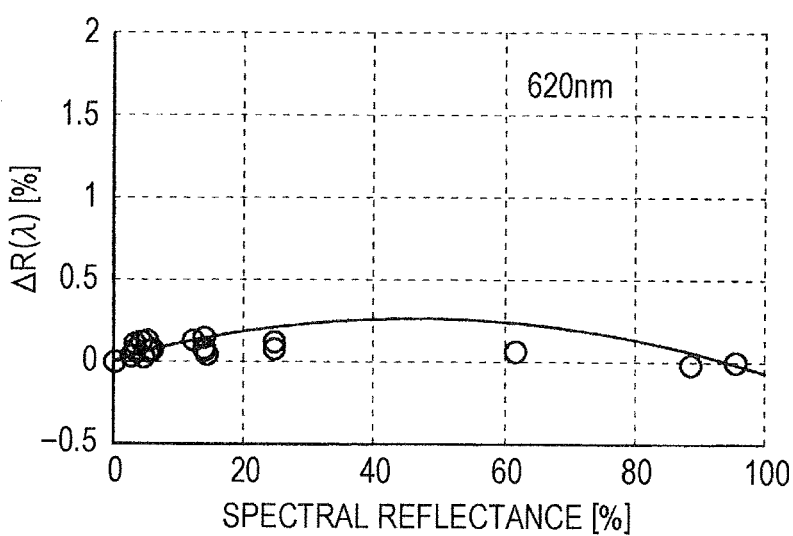
FIG. 26 is a diagram illustrating a relationship between a spectral reflectance and a spectral reflectance difference.
Figure 27:
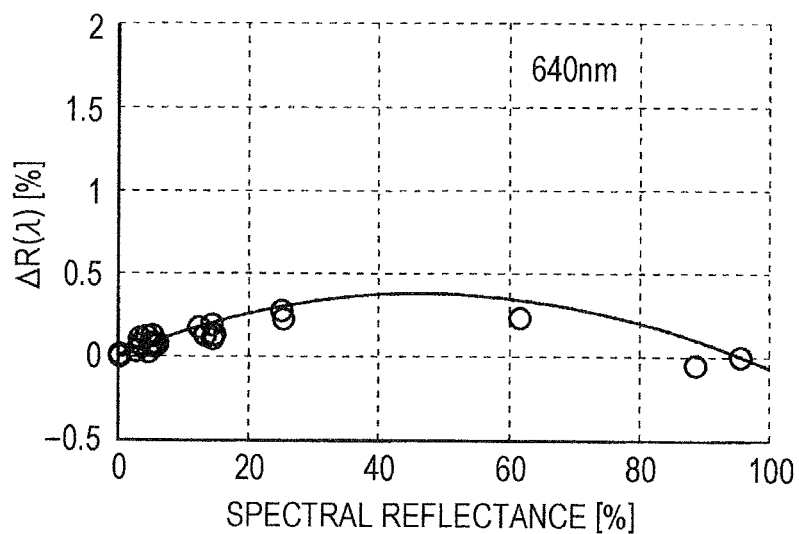
FIG. 27 is a diagram illustrating a relationship between a spectral reflectance and a spectral reflectance difference.
Figure 28:
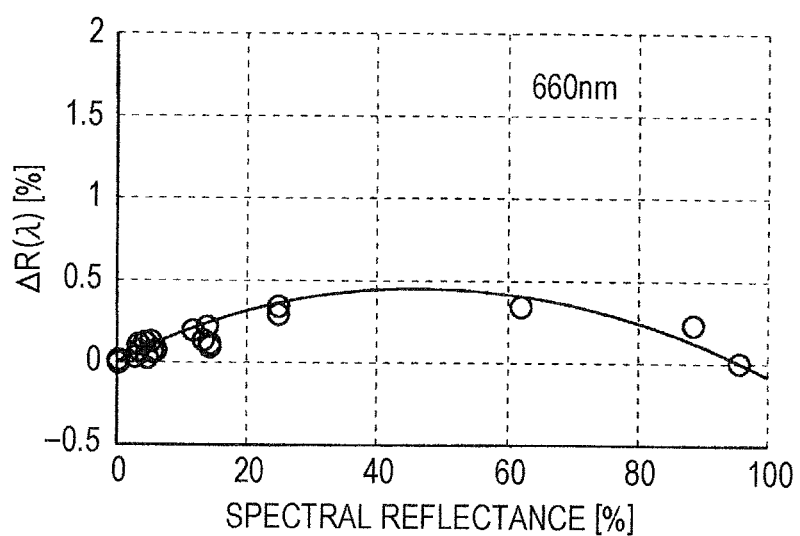
FIG. 28 is a diagram illustrating a relationship between a spectral reflectance and a spectral reflectance difference.
Figure 29:
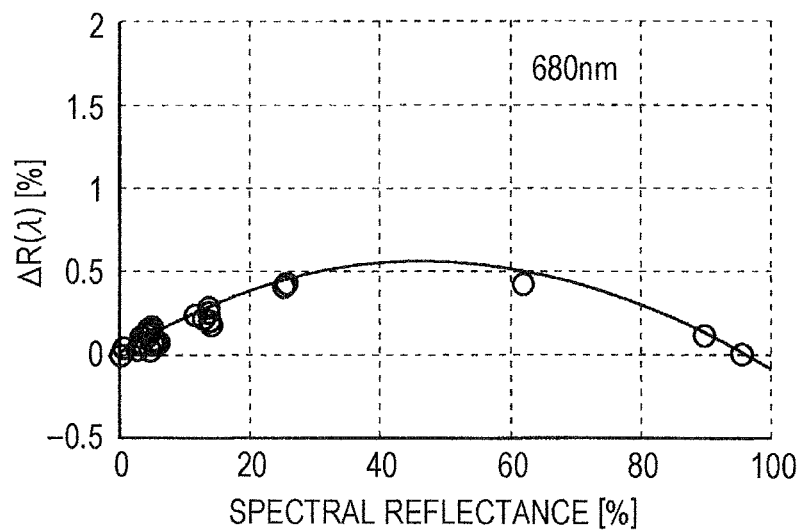
FIG. 29 is a diagram illustrating a relationship between a spectral reflectance and a spectral reflectance difference.
Figure 30:
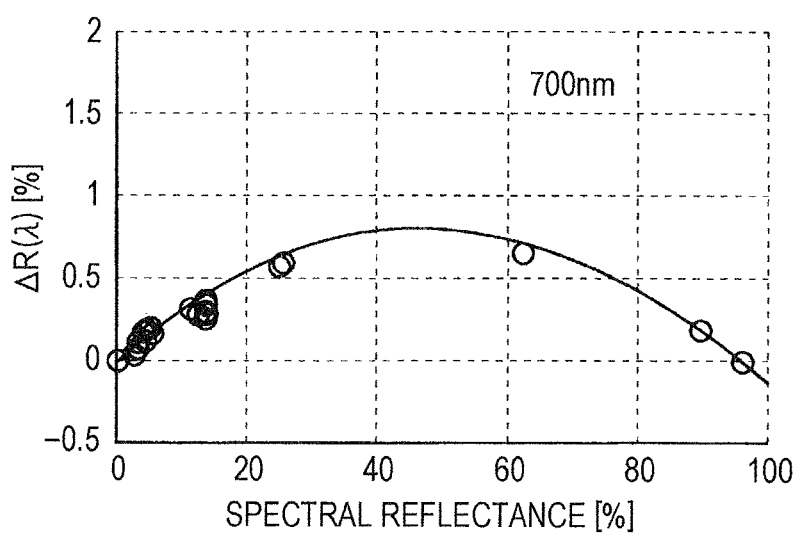
FIG. 30 is a diagram illustrating a relationship between a spectral reflectance and a spectral reflectance difference.
Figure 31:
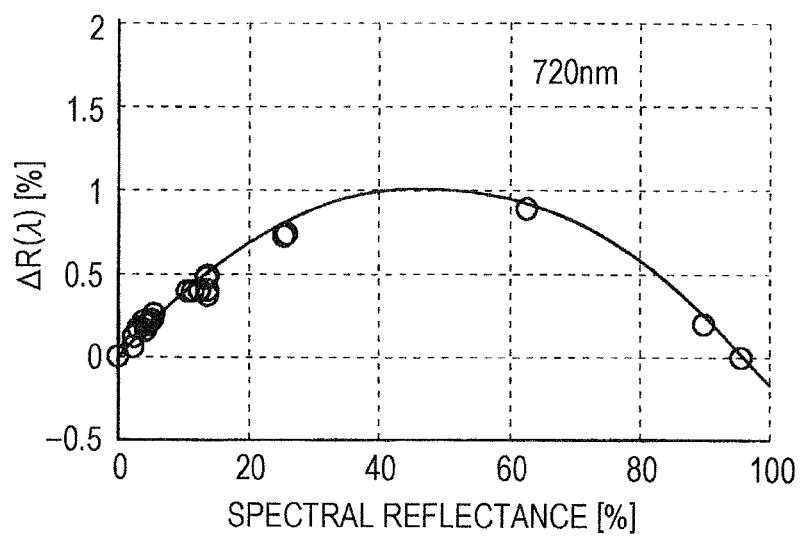
FIG. 31 is a diagram illustrating a relationship between a spectral reflectance and a spectral reflectance difference.
Figure 32:
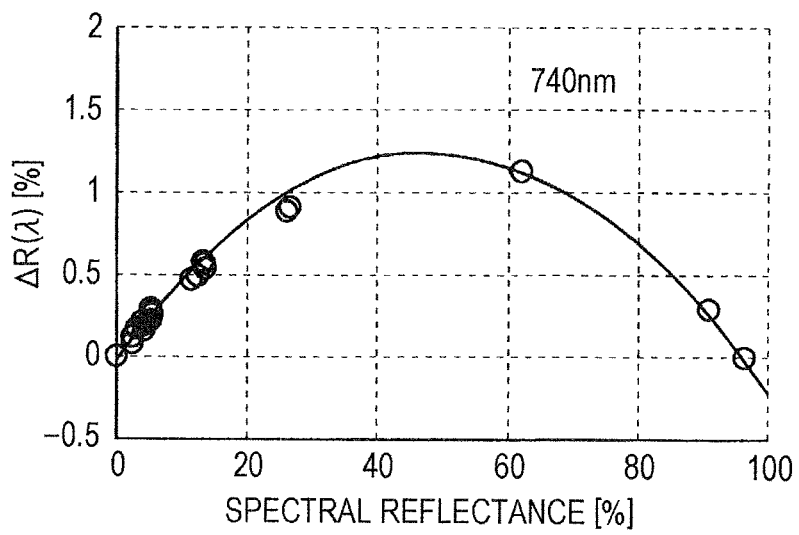
FIG. 32 is a diagram illustrating a relationship between a spectral reflectance and a spectral reflectance difference.

FIG. 12 is a diagram exemplifying a functional configuration realized by the control unit 14 of the first spectrocolorimetric device $1m$ in order to set the relationship information A1 as a first change rule for correcting the first deviation relating to the linearity between the devices.

As illustrated in FIG. 12, the control unit 14 of the first spectrocolorimetric device $1m$ is configured to include a calculation unit 14$ma$, an arithmetic unit 14$md$, and a setting unit 14$me$ as a functional configuration realized by executing the program P1 in the storage unit 15 by the processor P0.

The arithmetic unit 14$md$ acquires a relationship between the reflectance and the reflectance difference for each wavelength between a plurality of the first spectral reflectances acquired by measurement using the first spectrocolorimetric device $1m$ and a plurality of the second spectral reflectances acquired by measurement using the second spectrocolorimetric device $1t$. Herein, the plurality of first spectral reflectances can be acquired by measurement relating to a plurality of samples using the first spectrocolorimetric device $1m$, respectively. For example, with respect to each of the achromatic calibration samples, the calculation unit 14$ma$ can calculate the first spectral reflectance relating to the colorimetric object 100 on the basis of the spectroscopic spectrum relating to the reflected light from the colorimetric object 100 measured by the light-receiving unit 13 of the first spectrocolorimetric device 1m. In addition, the plurality of second spectral reflectances can be acquired by measurement relating to a plurality of samples using the second spectrocolorimetric device 1t, respectively. For example, with respect to each of the achromatic calibration samples, the calculation unit 14ta can calculate the second spectral reflectance relating to the colorimetric object 100 from the spectroscopic spectrum relating to the reflected light from the colorimetric object 100 measured by the light-receiving unit 13 of the second spectrocolorimetric device 1t.

The setting unit 14me sets the relationship information A1 as a conversion rule for converting the first spectral reflectance $R_m(\lambda)$ acquired by measurement using the first spectrocolorimetric device 1m to the second spectral reflectance $R_t(\lambda)$ that can be acquired by measurement using the second spectrocolorimetric device 1t on the basis of the relationship between the reflectance and the reflectance difference for each wavelength acquired by the arithmetic unit 14md.

FIGS. 13 to 32 are diagrams illustrating the relationships between the first spectral reflectance $R_m(\lambda)$ and the reflectance difference $\Delta R(\lambda)$. Herein, the first spectral reflectance $R_m(\lambda)$ is a measurement value acquired by actual measurement using the first spectrocolorimetric device 1m for plural types of achromatic calibration samples having different densities. The reflectance difference $\Delta R(\lambda)$ is the difference between the first spectral reflectance $R_m(\lambda)$ acquired by actual measurement using the first spectrocolorimetric device 1m and the second spectral reflectance $R_t(\lambda)$ acquired by actual measurement using the second spectrocolorimetric device 1t for each of the plural types of achromatic calibration samples having different densities.

FIGS. 13 to 32 illustrate the relationship between the first spectral reflectance $R_m(\lambda)$ and the reflectance difference $\Delta R(\lambda)$ for each wavelength $\lambda$ ($\lambda$=360, 380, 400, ..., 740 nm) at intervals of 20 nm in the range of 360 to 740 nm. In addition, in each of FIGS. 13 to 32, the data indicated by open circles are data obtained for wavelength ranges in which the spectral reflectance of each calibration sample is substantially constant. In addition, the curves drawn by solid lines approximately indicate the relationship between the first spectral reflectance $R_m(\lambda)$ and the reflectance difference $\Delta R(\lambda)$ for each wavelength. Herein, in the case where the first and second spectral reflectances $R_m(\lambda)$ and $R_t(\lambda)$ for each wavelength become about 50% by performing the white calibration and the black calibration in the first and second spectrocolorimetric devices 1m and 1t, respectively, the example where the reflectance difference $\Delta R(\lambda)$ exhibits a maximum value is illustrated.

On the other hand, with respect to the colorimetric object 100 which is dark and dark, the first spectral reflectance $R_m(\lambda)$ has a small value, and thus, an error due to measurement is likely to occur in the reflectance difference $\Delta R(\lambda)$. This error causes a decrease in the accuracy of correction in the case of correcting the first deviation relating to the linearity with respect to the chromatic colorimetric object 100 at the time of performing actual colorimetry not for calibration. For this reason, for the colorimetric object 100 having a small first spectral reflectance $R_m(\lambda)$, if the relationship between the first spectral reflectance $R_m(\lambda)$ and the reflectance difference $\Delta R(\lambda)$ is acquired while finely changing the first spectral reflectance $R_m(\lambda)$, the influence of the errors due to the measurement in the reflectance difference $\Delta R(\lambda)$ can be reduced.

For example, each of FIGS. 13 to 32 illustrates the mode where, with respect to the first spectral reflectance $R_m(\lambda)$ of 10% or less, the relationship between the first spectral reflectance $R_m(\lambda)$ and the reflectance difference $\Delta R(\lambda)$ for a plurality of colorimetric objects 100 having different densities is acquired by actual measurement. In addition, for example, with respect to the first spectral reflectance $R_m(\lambda)$ of above six levels such as 0, 5, 10, 20, 50, 100%, or the like, if the relationship between the first spectral reflectance $R_m(\lambda)$ and the reflectance difference $\Delta R(\lambda)$ is acquired by actual measurement, the error in the reflectance difference $\Delta R(\lambda)$ due to the measurement can be reduced to some extent. In addition, at this time, the spectral reflectance can be measured for a number of wavelengths corresponding to the number of the plurality of light-receiving elements by measurement for one calibration sample. Namely, data relating to a large number of spectral reflectances can be acquired by using a small number of calibration samples. As a result, the relationship information A1 for converting the first spectral reflectance $R_m(\lambda)$ to the second spectral reflectance $R_t(\lambda)$ can be easily acquired and set.

Herein, it is assumed that the relationship information A1 includes, for example, a relational formula approximately representing the relationship between the first spectral reflectance $R_m(\lambda)$ and the reflectance difference $\Delta R(\lambda)$ for each wavelength $\lambda$. Namely, it is assumed that the relational formula represents the relationship between the reflectance and the reflectance difference for each wavelength. Then, by fitting the function of the N-th order represented by Mathematical Formula (2) to the relationship between the first spectral reflectance $R_m(\lambda)$ and the reflectance difference $\Delta R(\lambda)$ obtained by actual measurement, the coefficient $a_n(\lambda)$ is obtained. In Mathematical Formula (2), n is an integer of 0 to N, and N is an arbitrary integer of 2 or more which can be appropriately set. Herein, as a fitting of the N-th order function, for example, calculation using a nonlinear least square method or the like may be employed. In addition, in the case where the first and second spectral reflectances $R_m(\lambda)$ and $R_t(\lambda)$ are configured with spectral reflectances for 39 wavelengths (360, 370, 380, ..., 740 nm) with a pitch of 10 nm in the wavelength range of 360 to 740 nm, respectively, the coefficient $a_n(\lambda)$ is obtained for each of the 39 wavelengths.

[Mathematical Formula 2]

$$\Delta R(\lambda) = \sum_{n=0}^{N} a_n(\lambda) \cdot \{R_m(\lambda)\}^n \qquad (2)$$

By such fitting, a relational formula approximately representing the relationship between the first spectral reflectance $R_m(\lambda)$ and the reflectance difference $\Delta R(\lambda)$ can be calculated. The calculation of the relational formula by fitting can be executed in the arithmetic unit 14md. However, the calculation of the relational formula by fitting may be executed by, for example, various types of information processing devices other than the first spectrocolorimetric device 1m.

Then, for example, the coefficient $a_n(\lambda)$ and Mathematical Formula (2) for each wavelength $\lambda$ obtained herein can be stored in the storage unit 15 as the relationship information A1 by the setting unit 14me. Namely, the setting unit 14me can set the relationship information A1 as the first conversion rule. Namely, the relationship information A1 may be set on the basis of the first and second spectral reflectances $R_m(\lambda)$ and $R_t(\lambda)$ respectively acquired by measurement using the first and second spectrocolorimetric devices 1m and 1*t* for each sample of achromatic calibration samples of which spectral reflectances are different from each other.

Accordingly, in the case where the first spectral reflectance $R_m(\lambda)$ is acquired by measurement using the first spectrocolorimetric device 1*m* for any colorimetric object 100, the reflectance difference $\Delta R(\lambda)$ corresponding to the first deviation relating to the linearity between the first and second spectrocolorimetric devices 1*m* and 1*t* can be calculated by inserting the first spectral reflectance $R_m(\lambda)$ into Mathematical Formula (2). Namely, the acquisition unit 14*mb* can acquire the reflectance difference $\Delta R(\lambda)$ for each wavelength $\lambda$ by calculation using the first spectral reflectance $R_m(\lambda)$ of an arbitrary colorimetric object 100 and the relational formula included in the relationship information A1. As a result, the conversion unit 14*mc* can convert the measurement value at a high accuracy and a high speed between the first and second spectrocolorimetric devices 1*m* and 1*t* which are different from each other.

Herein, for each wavelength $\lambda$, one N-th order function is fitted to a plurality of combinations of the first spectral reflectance $R_m(\lambda)$ and the reflectance difference $\Delta R(\lambda)$ obtained by actual measurement, but the present invention is not limited thereto.

For example, the first spectral reflectance $R_m(\lambda)$ may be divided into a plurality of regions, and an N-th function may be fitted to a plurality of combinations of the first spectral reflectance $R_m(\lambda)$ and the reflectance difference $\Delta R(\lambda)$ for each region. In this case, the relationship information A1 has a relational formula between the first spectral reflectance $R_m(\lambda)$ and the reflectance difference $\Delta R(\lambda)$ in each of the plurality of reflectance regions for each wavelength. In other words, for each wavelength $\lambda$, the coefficient $a_n(\lambda)$ in each of the plurality of reflectance regions may be calculated and stored in the storage unit 15. Herein, as the plurality of reflectance regions, a plurality of value ranges such as 0 to 10%, 10 to 50%, 50 to 100%, and the like which the region of 0 to 100% is divided into may be exemplified. Accordingly, the accuracy approximately indicating the relationship between the first spectral reflectance $R_m(\lambda)$ and the reflectance difference $\Delta R(\lambda)$ can be improved by the relational formula obtained by the fitting. Therefore, a highly-accurate conversion rule of measurement values between the different first and second spectrocolorimetric devices 1*m* and 1*t* can be more easily set.

For example, for each wavelength, a table indicating the relationship between the first spectral reflectance $R_m(\lambda)$ and the reflectance difference $\Delta R(\lambda)$ by a plurality of combinations of the reflectance and the reflectance difference may be stored as the relationship information A1 in the storage unit 15. In this case, for example, the acquisition unit 14*mb* can acquire the reflectance difference $\Delta R(\lambda)$ for each wavelength $\lambda$ on the basis of the first spectral reflectance $R_m(\lambda)$ of the arbitrary colorimetric object 100 and the table. As a result, the conversion unit 14*mc* can convert the measurement value at a high accuracy and a high speed between the first and second spectrocolorimetric devices 1*m* and 1*t* which are different from each other. In the case where such a configuration is employed, since the table indicating the relationship between the reflectance and the reflectance difference for each wavelength $\lambda$ can be easily set, a highly-accurate conversion rule of the measurement value between the first and second spectrocolorimetric devices 1*m* and 1*t* can be easily set.

With such a configuration, for example, the acquisition unit 14*mb* can acquire the reflectance difference $\Delta R(\lambda)$ for each wavelength $\lambda$ with respect to the first spectral reflectance $R_m(\lambda)$ relating to the arbitrary colorimetric object 100 by interpolation process using two or more combinations of the reflectance and the reflectance difference included in the table for each wavelength. Therefore, it is possible to realize a reduction in the storage capacity of the storage unit 15 and a reduction in the number of calibration samples and the number of times of measurement to obtain a large number of combinations of the reflectance and the reflectance difference. Namely, since the data indicating the relationship between the reflectance and the reflectance difference for each wavelength can be reduced, the data can be easily acquired. As a result, a highly-accurate conversion rule of measurement values between the first and second spectrocolorimetric devices 1*m* and 1*t* which are different from each other can be easily set.

Herein, for example, in the table of each wavelength, an example is assumed where the relationship between the reflectance and the reflectance difference is described for six reflectances of 0, 5, 10, 20, 50, and 100%. In this example, for example, if 15% is acquired as the first spectral reflectance $R_m(\lambda)$ of an arbitrary colorimetric object 100 by measurement using the first spectrocolorimetric device 1*m*, the reflectance difference corresponding to the reflectance of 15% can be acquired by an interpolation process using two combinations of reflectance and reflectance difference for two levels of reflectance of 10% and 20% in the table for each wavelength.

In addition, for example, if an example of storing combinations of the reflectances and the reflectance differences relating to a large number of spectral reflectances with fine pitches in a table for each wavelength is assumed, the storage capacity of the storage unit 15, the number of calibration samples for obtaining a large number of combinations of the reflectance and the reflectance difference, and the number of times of measurement thereof, and the like can be increased. However, it is possible to reduce the calculation load and to improve the calculation speed, for example, by omitting the interpolation process.

On the other hand, for example, even though the colorimetric object 100 is chromatic, in the case where the spectral reflectance is gently changed with respect to the change in wavelength in the colorimetric object 100, the second deviation relating to the spectral sensitivity between the devices is small. Therefore, in such a case, by correcting the first deviation relating to linearity with respect to the first spectral reflectance $R_m(\lambda)$ acquired by measurement using the first spectrocolorimetric device 1*m* in accordance with Mathematical Formula (3), the first spectral reflectance $R_m(\lambda)$ can be converted to the second spectral reflectance $R_t(\lambda)$.

[Mathematical Formula 3]

$$R_t(\lambda) \approx R_m(\lambda) - \Delta R(\lambda) \quad (3)$$

Figure 33:
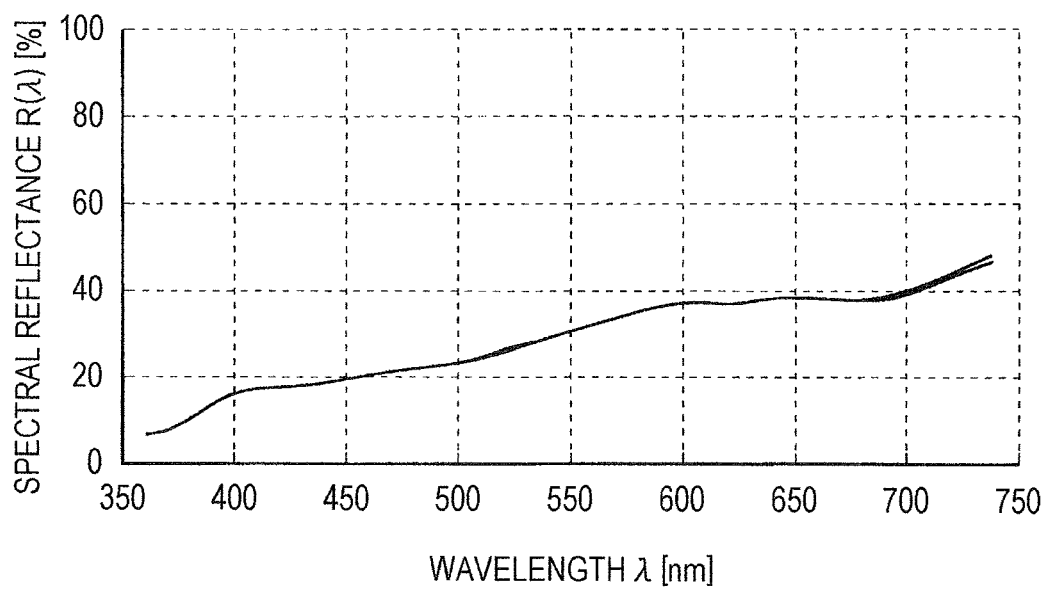
FIG. 33 is a diagram exemplifying first and second spectral reflectances acquired by measurement using first and second spectrocolorimetric devices.

FIG. 33 is a diagram exemplifying first and second spectral reflectances $R_m(\lambda)$ and $R_t(\lambda)$ respectively acquired by measurement using the first and second spectrocolorimetric devices 1*m* and 1*t*. In FIG. 33, the first and second spectral reflectances $R_m(\lambda)$ and $R_t(\lambda)$ for the colorimetric object 100 of which change in spectral reflectance with respect to the change in wavelength $\lambda$ is gentle are exemplified.

Figure 34:
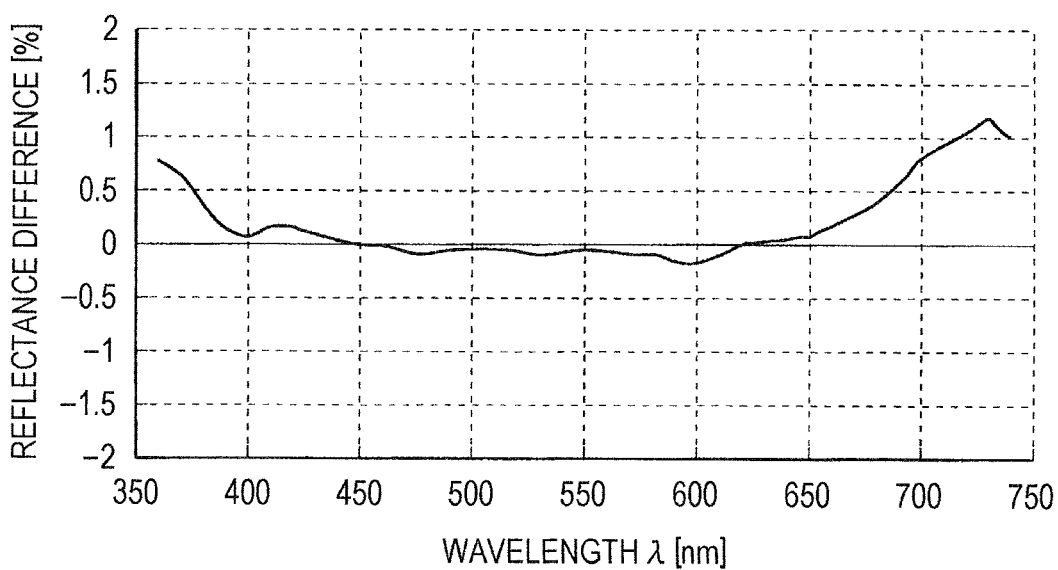
FIG. 34 is a diagram exemplifying a difference between first and second spectral reflectances.

FIG. 34 is a diagram exemplifying the difference between the first spectral reflectance $R_m(\lambda)$ acquired by measurement using the first spectrocolorimetric device 1*m* and the second spectral reflectance $R_t(\lambda)$ acquired by measurement using the second spectrocolorimetric device 1*t* for the colorimetric object 100 of which the spectral reflectance is gently changed with respect to a change in wavelength $\lambda$. As illustrated in FIG. 34, even when the colorimetric object 100 has a gentle change in spectral reflectance with respect to a change in wavelength λ, the difference between the first spectral reflectance $R_m(λ)$ and the second spectral reflectance $R_t(λ)$ occurs to some extent.

Figure 35:
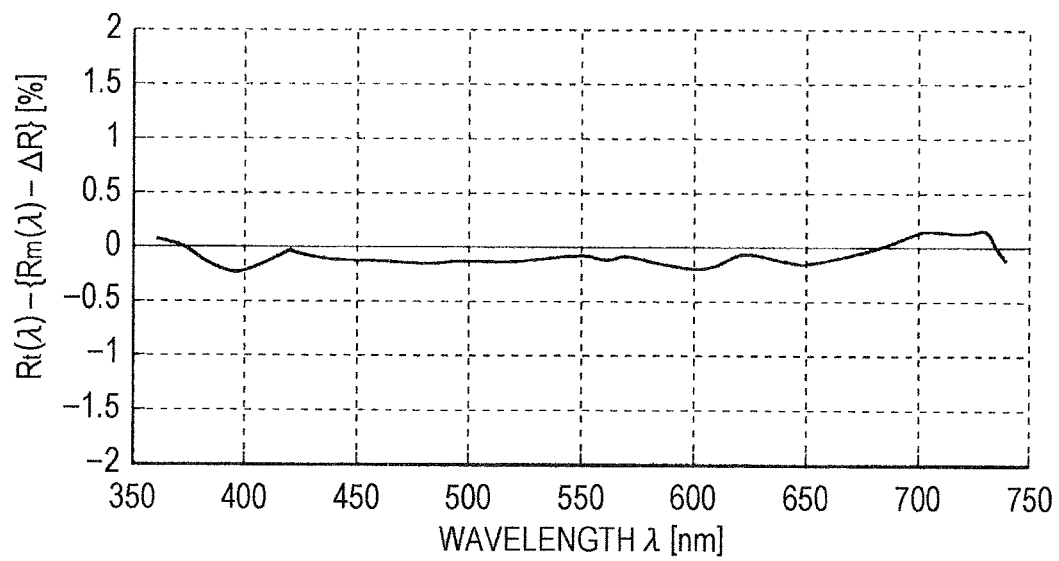
FIG. 35 is a diagram exemplifying a difference between a corrected first spectral reflectance obtained by subtracting a reflectance difference from the first spectral reflectance and a second spectral reflectance.

FIG. 35 is a diagram exemplifying a difference between a corrected first spectral reflectance (first spectral reflectance $R_m(λ)-ΔR(λ))$ obtained by subtracting the reflectance difference $ΔR(λ)$ from the first spectral reflectance $R_m(λ)$ and the second spectral reflectance $R_t(λ)$ for the colorimetric object 100 having a gentle change in spectral reflectance with respect to a change in wavelength λ. Herein, the reflectance difference $ΔR(λ)$ is acquired by the acquisition unit 14mb on the basis of the first spectral reflectance $R_m(λ)$ relating to the colorimetric object 100 and the relationship information A1. As illustrated in FIG. 35, for the colorimetric object 100 having a gentle change in spectral reflectance with respect to a change in wavelength λ, if the first deviation relating to the linearity is corrected, a deviation in spectral reflectance between the first and second spectrocolorimetric devices 1m and 1t can be sufficiently reduced.

In addition, as illustrated in FIG. 4, there are few colorimetric objects 100 of which spectral reflectance is abruptly changed with respect to a change in wavelength λ. For this reason, even though the second deviation relating to the spectral sensitivity is not corrected, if the first deviation relating to the linearity is corrected, in many cases, the deviation of spectral reflectance between the first and second spectrocolorimetric devices 1m and 1t is sufficiently reduced.

Figure 36:
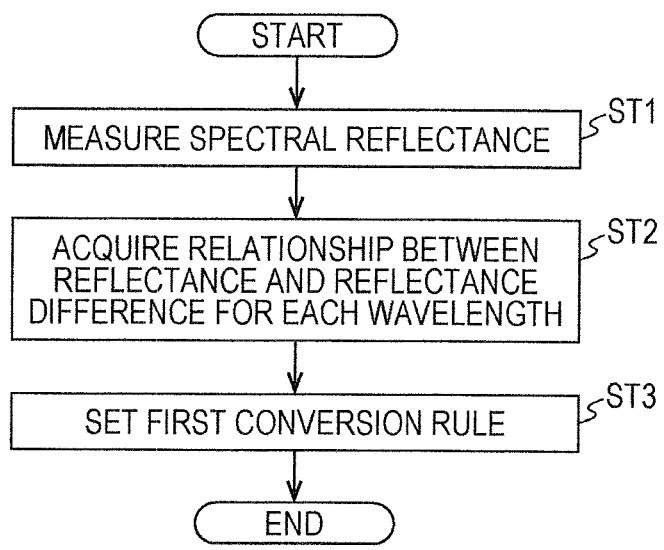
FIG. 36 is a flowchart illustrating an operation flow relating to setting of conversion rules.

FIG. 36 is a flowchart illustrating an operation flow of setting the relationship information A1 as the first conversion rule for correcting the first deviation relating to the linearity.

First, in step ST1, the spectral reflectance of each of the plurality of samples is measured by the first and second spectrocolorimetric devices 1m and 1t. Herein, the plurality of samples are, for example, a plurality of achromatic calibration samples having different spectral reflectances. In the first spectrocolorimetric device 1m, for example, with respect to each achromatic calibration sample, the spectroscopic spectrum relating to the reflected light from the colorimetric object 100 is measured by the light-receiving unit 13, and the first spectral reflectance $R_m(λ)$ of the colorimetric object 100 can be calculated from the spectroscopic spectrum by the calculation unit 14ma. In addition, in the second spectrocolorimetric device 1t, for example, with respect to each achromatic calibration sample, the spectroscopic spectrum relating to reflected light from the colorimetric object 100 is measured by the light-receiving unit 13, and the second spectral reflectance $R_t(λ)$ of the colorimetric object 100 can be calculated from the spectroscopic spectrum by the calculation unit 14ta.

Next, in step ST2, on the basis of the measurement result in step ST1, the arithmetic unit 14md acquires the relationship between the reflectance for each wavelength and the reflectance difference as a deviation component relating to the reflectance between the plurality of first spectral reflectances $R_m(λ)$ and the plurality of second spectral reflectances $R_t(λ)$.

Next, in step ST3, the setting unit 14me sets the relationship information A1 as the first conversion rule. Herein, the relationship information A1 is set as a first conversion rule that converts the first spectral reflectance $R_m(λ)$ to the second spectral reflectance $R_t(λ)$ on the basis of the relationship between the reflectance and the reflectance difference for each wavelength acquired in step ST2.

By such an operation flow, the relationship between the reflectance and the reflectance difference for each wavelength can be easily obtained. For this reason, a highly-accurate conversion rule of measurement values between the first and second spectrocolorimetric devices 1m and 1t which are different from each other can be easily set.

As described above, the first spectral reflectance $R_m(λ)$ is converted into the second spectral reflectance $R_t(λ)$ that can be acquired by measurement using the second spectrocolorimetric device 1t on the basis of the relationship between the reflectance and the reflectance difference for each wavelength and the first spectral reflectance $R_m(λ)$ calculated from the spectroscopic spectrum acquired by measurement. Therefore, the first deviation relating to the linearity between the devices can be corrected. Then, herein, separately from the second deviation relating to the spectral sensitivity, the relationship between the reflectance and the reflectance difference for each wavelength is set. For this reason, a highly-accurate conversion rule of measurement values between the first and second spectrocolorimetric devices 1m and 1t which are different from each other can be easily set.

<(1-4-2) Correction of Deviation (Second Deviation) Relating to Spectral Sensitivity Between Devices>

As illustrated in FIG. 4, in the case where the spectral reflectance of the colorimetric object 100 is abruptly changed with respect to a change in wavelength, the deviation in spectral reflectance due to the second deviation relating to the spectral sensitivity occurs. Therefore, if the second deviation relating to the spectral sensitivity between the devices is corrected, the deviation in spectral reflectance between the devices can be sufficiently reduced.

Herein, a method of correcting both of the first deviation relating to the linearity between the devices and the second deviation relating to the spectral sensitivity between the devices will be described. However, in the case where the optical systems or the like are not different between the devices and the first deviation relating to the linearity hardly occurs, for example, the second deviation relating to the spectral sensitivity may be corrected without correcting the first deviation relating to the linearity between the devices.

An intensity (also referred to as a spectroscopic spectrum) of the light having the wavelength λ of the incident light L0 incident from the colorimetric object 100 through the slit portion 131s into the light-receiving unit 13 in the first spectrocolorimetric device 1m is denoted by $L(λ)$. A spectral sensitivity of the k-th light-receiving element (k is a natural number of 1 to K0) of the sensor unit 133 of the first spectrocolorimetric device 1m is denoted by $s_m(k,λ)$, and a center wavelength of the light received by the k-th light-receiving element is denoted by $λ_{G\_m}(k)$. At this time, an intermediate wavelength (also referred to as an intermediate wavelength) $λ_{B\_m}(k)$ between the center wavelength $λ_{G\_m}(k-1)$ of the light received by the (k-1)-th light-receiving element and the center wavelength $λ_{G\_m}(k)$ of the light received by the k-th light-receiving element in the sensor unit 133 of the first spectrocolorimetric device 1m is represented by Mathematical Formula (4).

[Mathematical Formula 4]

$$λ_{B\_m}(k) = \frac{λ_{G\_m}(k-1) + λ_{G\_m}(k)}{2} \qquad (4)$$

Then, a signal (also referred to as a first output signal) $C_m(k)$ output according to the intensity of light at the k-th light-receiving element in the sensor unit 133 of the first spectrocolorimetric device 1m is represented by Mathematical Formula (5).

[Mathematical Formula 5]

$$G_m(k) = \int_0^\infty s_m(k, \lambda) \cdot L(\lambda) \cdot d\lambda \qquad (5)$$

$$\cong \sum_{j=1}^{K_0} L(\lambda_{G\_m}(j)) \cdot \int_{\lambda_{B\_m}(j)}^{\lambda_{B\_m}(j+1)} s_m(k, \lambda) \cdot d\lambda$$

$$= \sum_{j=1}^{K_0} L(\lambda_{G\_m}(j)) \cdot S_m(k, j)$$

Mathematical Formula (5) can be rewritten as a determinant as represented in Mathematical Formula (6).

[Mathematical Formula 6]

$$\begin{pmatrix} G_m(1) \\ \vdots \\ G_m(K_0) \end{pmatrix} = \begin{pmatrix} S_m(1,1) & \cdots & S_m(1, K_0) \\ \vdots & \ddots & \vdots \\ S_m(K_0, 1) & \cdots & S_m(K_0, K_0) \end{pmatrix} \cdot \begin{pmatrix} L(\lambda_{G\_m}(1)) \\ \vdots \\ L(\lambda_{G\_m}(K_0)) \end{pmatrix} \qquad (6)$$

provided that, $$S_m(k, j) = \int_{\lambda_{B\_m}(j)}^{\lambda_{B\_m}(j+1)} s_m(k, \lambda) \cdot d\lambda$$

Then, in the k-th light-receiving element in the sensor unit 133 of the first spectrocolorimetric device 1m, the first output signal $C_m(k)$ is output in response to the incidence of the incident light L0 having the spectroscopic spectrum $L(\lambda)$. At this time, the light intensity (also referred to as a first spectroscopic spectrum) $L(\lambda_{G\_m}(k))$ at the wavelength $\lambda_{G\_m}(k)$ of the incident light L0 is calculated by inserting the first output signal $C_m(k)$ into Mathematical Formula (7).

[Mathematical Formula 7]

$$\begin{pmatrix} L(\lambda_{G\_m}(1)) \\ \vdots \\ L(\lambda_{G\_m}(K_0)) \end{pmatrix} = \begin{pmatrix} S_m(1,1) & \cdots & S_m(1, K_0) \\ \vdots & \ddots & \vdots \\ S_m(K_0, 1) & \cdots & S_m(K_0, K_0) \end{pmatrix}^{-1} \cdot \begin{pmatrix} G_m(1) \\ \vdots \\ G_m(K_0) \end{pmatrix} \qquad (7)$$

Herein, if an accurate spectral sensitivity $s_m(k,\lambda)$ of the first spectrocolorimetric device 1m is obtained, the first spectroscopic spectrum $L(\lambda_{G\_m}(k))$ relating to the incident light L0 is accurately obtained by Mathematical Formula (7). For example, if the first spectrocolorimetric device 1m is a product of a certain manufacturer, the spectral sensitivity $s_m(k,\lambda)$ at the light-receiving unit 13 of the first spectrocolorimetric device 1m can be accurately obtained by the certain manufacturer. For example, in the case where the output signals from the light-receiving elements are directly obtained in the first spectrocolorimetric device 1m, the output signals output from the light-receiving elements of the first spectrocolorimetric device 1m according to the light of the specific wavelength may be obtained, so that the spectral sensitivity $s_m(k,\lambda)$ may be calculated. Herein, as the light having the specific wavelength, for example, at least one of monochromatic light emitted from the monochromator and light having a plurality of specific wavelengths emitted from the bright-line light source may be employed.

In addition, herein, it is assumed that the incident light L0 having the same spectroscopic spectrum $L(\lambda)$ as the incident light on the light-receiving unit 13 of the first spectrocolorimetric device 1m is also incident on the light-receiving unit 13 of the second spectrocolorimetric device 1t. In addition, a true spectral sensitivity of the k-th light-receiving element in the sensor unit 133 of the second spectrocolorimetric device 1t is denoted by $s_t(k,\lambda)$, and a center wavelength of light received by the k-th light-receiving element is denoted by $\lambda_{G\_t}(k)$.

At this time, an intermediate wavelength (also referred to as an intermediate wavelength) $\lambda_{B\_t}(k)$ between the center wavelength $\lambda_{G\_t}(k-1)$ of the light received by the (k−1)-th light-receiving element in the sensor unit 133 and the center wavelength of $\lambda_{G\_t}(k)$ of the light received by the k-th light-receiving element is represented by Mathematical Formula (8).

[Mathematical Formula 8]

$$\lambda_{G\_t}(k) = \frac{\lambda_{G\_t}(k-1) + \lambda_{G\_t}(k)}{2} \qquad (8)$$

Herein, the intensity $L(\lambda_{G\_t}(k))$ of the incident light L0 at the center wavelength $\lambda_{G\_t}(k)$ is obtained by an interpolation process using, for example, the intensity $L(\lambda_{G\_m}(k))$ of the incident light L0 at two adjacent wavelengths $\lambda_{G\_m}(k)$ interposing the center wavelength $\lambda_{G\_t}(k)$.

In addition, in this case, for example, if the second spectrocolorimetric device 1t is a product of a certain manufacturer, the true spectral sensitivity $s_t(k,\lambda)$ at the light-receiving unit 13 of the second spectrocolorimetric device 1t can be accurately obtained by the certain manufacturer. For example, in the case where the output signals from the light-receiving elements are directly obtained in the second spectrocolorimetric device 1t, the output signals output from the light-receiving elements of the second spectrocolorimetric device 1t according to the light of the specific wavelength are obtained, so that the spectral sensitivity $s_t(k,\lambda)$ may be obtained. Herein, as the light having the specific wavelength, for example, at least one of monochromatic light emitted from the monochromator and light having a plurality of specific wavelengths emitted from the bright-line light source may be employed. In addition, the spectral sensitivity $s_t(k,\lambda)$ may be obtained by, for example, optical simulation.

In addition, herein, it is assumed that the incident light L0 having the same spectroscopic spectrum $L(\lambda)$ as the incident light on the light-receiving unit 13 of the first spectrocolorimetric device 1m is incident on the light-receiving unit 13 of the second spectrocolorimetric device 1t. In this case, the estimated value (also referred to as a second estimated output signal) $C_t(k)$ of the output signal that can be output according to the intensity of light by the k-th light-receiving element in the sensor unit 133 of the second spectrocolorimetric device 1t can be calculated by Mathematical Formula (9).

[Mathematical Formula 9]

$$C_t(k) = \int_0^\infty s_t(k, \lambda) \cdot L(\lambda) \cdot d\lambda \quad (9)$$

$$\cong \sum_{j=1}^{K_0} L(\lambda_{G\_t}(j)) \cdot \int_{\lambda_{B\_t}(j)}^{\lambda_{B\_t}(j+1)} s_t(k, \lambda) \cdot d\lambda$$

$$= \sum_{j=1}^{K_0} L(\lambda_{G\_t}(j)) \cdot S_t(k, \lambda)$$

Mathematical Formula (9) can be rewritten as a determinant as represented in Mathematical Formula (10).

[Mathematical Formula 10]

$$\begin{pmatrix} C_t(1) \\ \vdots \\ C_t(K_0) \end{pmatrix} = \begin{pmatrix} S_t(1,1) & \cdots & S_t(1, K_0) \\ \vdots & \ddots & \vdots \\ S_t(K_0, 1) & \cdots & S_t(K_0, K_0) \end{pmatrix} \cdot \begin{pmatrix} L(\lambda_{G\_t}(1)) \\ \vdots \\ L(\lambda_{G\_t}(K_0)) \end{pmatrix} \quad (10)$$

provided that, $$S_t(k, j) = \int_{\lambda_{B\_t}(j)}^{\lambda_{B\_t}(j+1)} s_t(k, \lambda) \cdot d\lambda$$

Herein, with respect to the k-th light-receiving element in the sensor unit 133 of the second spectrocolorimetric device 1t, the calibrated spectral sensitivity (also referred to as a calibrated spectral sensitivity) obtained by calibration of the wavelength in the second spectrocolorimetric device 1t is denoted by $s^*_t(k,\lambda)$. In addition, at this time, the calibrated center wavelength (also referred to as a calibrated center wavelength) of light received by the k-th light-receiving element is denoted by $\lambda^*_{G\_t}(k)$. The calibrated spectral sensitivity $s^*_t(k,\lambda)$ may be a spectral sensitivity deviated from the true spectral sensitivity $s_t(k,\lambda)$ depending on an accuracy of a wavelength calibration method in the second spectrocolorimetric device 1t.

In addition, an intermediate wavelength (also referred to as a calibrated intermediate wavelength) $\lambda^*_{B\_t}(k)$ between the calibrated center wavelength $\lambda^*_{G\_t}(k-1)$ of the light received by the (k-1)-th light-receiving element and the calibrated center wavelength $\lambda^*_{G\_t}(k)$ of the light received by the k-th light-receiving element in the sensor unit 133 of the second spectrocolorimetric device 1t is represented by Mathematical Formula (11).

[Mathematical Formula 11]

$$\lambda^*_{B\_t}(k) = \frac{\lambda^*_{G\_t}(k-1) + \lambda^*_{G\_t}(k)}{2} \quad (11)$$

By inserting the second estimated output signal $C_t(k)$ obtained by Mathematical Formula (10) into Mathematical Formula (12), the estimated value (also referred to as a second estimated spectroscopic spectrum) $L^*(\lambda^*_{G\_t}(k))$ of the calibrated strength of the incident light L0 can be calculated.

[Mathematical Formula 12]

$$\begin{pmatrix} L^*(\lambda^*_{G\_t}(1)) \\ \vdots \\ L^*(\lambda^*_{G\_t}(K_0)) \end{pmatrix} = \begin{pmatrix} S^*_t(1,1) & \cdots & S^*_t(1, K_0) \\ \vdots & \ddots & \vdots \\ S^*_t(K_0, 1) & \cdots & S^*_t(K_0, K_0) \end{pmatrix}^{-1} \cdot \begin{pmatrix} C_t(1) \\ \vdots \\ C_t(K_0) \end{pmatrix} \quad (12)$$

provided that, $$S^*_t(k, j) = \int_{\lambda^*_{B\_t}(j)}^{\lambda^*_{B\_t}(j+1)} s^*_t(k, \lambda) \cdot d\lambda$$

Namely, by sequentially performing the following Steps 1 to 3, the second estimated spectroscopic spectrum $L^*(\lambda^*_{G\_t}(k))$ relating to the incident light L0 can be acquired.

[Step 1] As represented in Mathematical Formula (7), the spectroscopic spectrum $L(\lambda)$ of the incident light L0 is calculated by a product of the inverse matrix relating to the spectral sensitivity $s_m(k,\lambda)$ and the column vector of the output signal $C_m(k)$ according to the incident light L0 acquired by actual measurement using the first spectrocolorimetric device 1m.

[Step 2] As represented in Mathematical Formula (10), the column vector of the second estimated output signal $C_t(k)$ that can be acquired by the second spectrocolorimetric device 1t is calculated by a product of the matrix relating to the true spectral sensitivity $s_t(k,\lambda)$ of the second spectrocolorimetric device 1t and the column vector of the spectroscopic spectrum $L(\lambda)$ of the incident light L0 calculated in Step 1. Herein, the second estimated output signal $C_t(k)$ is an estimated value of the output signal that is estimated to be acquired by measurement using the second spectrocolorimetric device 1t when the incident light L0 is incident on the light-receiving unit 13 of the second spectrocolorimetric device 1t. However, it is assumed that the spectroscopic spectrum $L(\lambda)$ of the incident light L0 incident on the light-receiving unit 13 of the second spectrocolorimetric device 1t is the same as the spectroscopic spectrum $L(\lambda)$ of the incident light L0 incident on the light-receiving unit 13 of the first spectrocolorimetric device 1m.

[Step 3] As represented in Mathematical Formula (12), the second estimated spectroscopic spectrum $L^*(\lambda^*_{G\_t}(k))$ is calculated by a product of the inverse matrix of the calibrated spectral sensitivity $s^*_t(k,\lambda)$ of the second spectrocolorimetric device 1t and the column vector of the second estimated output signal $C_t(k)$ acquired in Step 2. The second estimated spectroscopic spectrum $L^*(\lambda^*_{G\_t}(k))$ is an estimated value of the spectroscopic spectrum of the incident light L0 that can be acquired by measurement using the second spectrocolorimetric device 1t.

In addition, it is assumed that the incident light L0 having the same spectroscopic spectrum as the incident light L0 incident on the light-receiving unit 13 of the first spectrocolorimetric device 1m is incident on the light-receiving unit 13 of the second spectrocolorimetric device 1t. Therefore, the estimated value (also referred to as the second estimated spectral reflectance) $R^*(\lambda^*_{G\_t}(k))$ of the second spectral reflectance of the colorimetric object 100 that can be acquired by measurement using the second spectrocolorimetric device 1t can be calculated by Mathematical Formula (13).

[Mathematical Formula 13]

$$R_t^*(\lambda_{G\_t}^*(k)) = \frac{L_{Sample}^*(\lambda_{G\_T}^*(k)) - L_{Black}^*(\lambda_{G\_t}^*(k))}{L_{White}^*(\lambda_{G\_t}^*(k)) - L_{Black}^*(\lambda_{G\_t}^*(k))} \times R_{White}(\lambda_{G\_t}^*(k))0 - \Delta R(\lambda_{G\_t}^*(k)) \quad (13)$$

In Mathematical Formula (13), the second estimated spectral reflectance $R^*_t(\lambda^*_{G\_t}(k))$ is represented as a value obtained by subtracting the second term on the right hand side according to the first deviation relating to the linearity from the first term on the right hand side according to the second deviation relating to the spectral sensitivity. Herein, the first term on the right hand side is changed according to the second deviation relating to the spectral sensitivity due to the accuracy of the wavelength calibration method in the second spectrocolorimetric device $1t$. In addition, the second term on the right hand side indicates the reflectance difference $\Delta R(\lambda^*_{G\_t}(k))$ as the first deviation relating to the linearity in the spectral reflectance.

Herein, with respect to the first term on the right hand side of Mathematical Formula (13), $L^*_{White}(\lambda^*_{G\_t}(k))$ is a second estimated spectroscopic spectrum (also referred to as a second white estimated spectroscopic spectrum) relating to the white calibration plate. $L^*_{Black}(\lambda^*_{G\_t}(k))$ is the second estimated spectroscopic spectrum (also referred to as second black estimated spectroscopic spectrum) relating to the black calibration plate. $L^*_{Sample}(\lambda^*_{G\_t}(k))$ is a second estimated spectroscopic spectrum (also referred to as a second object estimated spectroscopic spectrum) relating to the colorimetric object 100. In addition, $R_{White}(\lambda^*_{G\_t}(k))$ is a second spectral reflectance (also referred to as a second white spectral reflectance) relating to the white calibration plate.

The second white estimated spectroscopic spectrum $L^*_{White}(\lambda^*_{G\_t}(k))$, the second black estimated spectroscopic spectrum $L^*_{Black}(\lambda^*_{G\_t}(k))$, and the second object estimated spectroscopic spectrum $L^*_{Sample}(\lambda^*_{G\_t}(k))$ can be calculated, for example, by performing the measurement and calculation according to the above-described Steps 1 to 3 with respect to the white calibration plate, the black calibration plate, and the colorimetric object 100. Specifically, with respect to the white calibration plate, the second white estimated spectroscopic spectrum $L^*_{White}(\lambda^*_{G\_t}(k))$ is calculated on the basis of the first output signal $C_m(k)$ obtained by actual measurement using the first spectrocolorimetric device $1m$ and Mathematical Formulas (7), (10), and (12). With respect to the black calibration plate, the second black estimated spectroscopic spectrum $L^*_{Black}(\lambda^*_{G\_t}(k))$ is calculated on the basis of the first output signal $C_m(k)$ obtained by actual measurement using the first spectrocolorimetric device $1m$ and Mathematical Formulas (7), (10), and (12). The second object estimated spectroscopic spectrum $L^*_{Sample}(\lambda^*_{G\_t}(k))$ is calculated by the first output signal $C_m(k)$ obtained by the actual measurement using the first spectrocolorimetric device $1m$ for the colorimetric object 100 and Mathematical Formulas (7), (10) and (12).

For example, the second white spectral reflectance $R_{White}(\lambda^*_{G\_t}(k))$ may be preset for the white calibration plate.

In addition, the reflectance difference $\Delta R(\lambda^*_{G\_t}(k))$ of the second term on the right hand side of Mathematical Formula (13) can be acquired by, for example, using the method described in Section (1-4-1) on the basis of the first spectral reflectance $R_m(\lambda^*_{G\_t}(k))$ acquired by measurement using the first spectrocolorimetric device $1m$ for the colorimetric object 100 and the relationship information A1. In addition, the relationship information A1 can also be set, for example, by the method described in the above Section (1-4-1).

The first spectral reflectance $R_m(\lambda^*_{G\_t}(k))$ can be calculated by Mathematical Formula (14).

[Mathematical Formula 14]

$$Rm(\lambda_{G\_t}^*(k)) = \frac{L_{Sample}(\lambda_{G\_t}^*(k)) - L_{Black}(\lambda_{G\_t}^*(k))}{L_{White}(\lambda_{G\_t}^*(k)) - L_{Black}(\lambda_{G\_T}^*(k))} \times R_{White}(\lambda_{G\_t}^*(k)) \quad (14)$$

In Mathematical Formula (14), $L_{White}(\lambda^*_{G\_t}(k))$ is a spectroscopic spectrum (also referred to as a second white spectroscopic spectrum) that can be acquired by measurement using the second spectrocolorimetric device $1t$ for the white calibration plate. $L_{Black}(\lambda^*_{G\_t}(k))$ is a spectroscopic spectrum (also referred to as a second black spectroscopic spectrum) that can be acquired by measurement using the second spectrocolorimetric device $1t$ with respect to the black calibration plate. $L_{Sample}(\lambda^*_{G\_t}(k))$ is a spectroscopic spectrum (also referred to as a second object spectroscopic spectrum) that can be acquired by measurement using the second spectrocolorimetric device $1t$ for the colorimetric object 100. In addition, $R_{White}(\lambda^*_{G\_t}(k))$ is the second spectral reflectance (second white spectral reflectance) relating to the white calibration plate. In addition, herein, the spectral reflectance of the black calibration plate is treated as 0%.

Herein, for example, the spectroscopic spectrum (also referred to as a first white spectroscopic spectrum) $L_{White}(\lambda_{G\_m}(k))$ relating to the white calibration plate can be acquired by applying the first output signal $C_m(k)$ acquired by measurement using the first spectrocolorimetric device $1m$ for the white calibration plate to Mathematical Formula (7). Then, the second white spectroscopic spectrum $L_{White}(\lambda^*_{G\_t}(k))$ can be acquired by interpolation operation of the first white spectroscopic spectrum $L_{White}(\lambda_{G\_m}(k))$.

In addition, for example, the spectroscopic spectrum (also referred to as a first black spectroscopic spectrum) $L_{Black}(\lambda_{G\_m}(k))$ of the black calibration plate can be obtained by applying the first output signal $C_m(k)$ acquired by measurement using the first spectrocolorimetric device $1m$ for the black calibration plate to Mathematical Formula (7). Then, the second black spectroscopic spectrum $L_{Black}(\lambda^*_{G\_t}(k))$ can be acquired by an interpolation operation of the first black spectroscopic spectrum $L_{Black}(\lambda_{G\_m}(k))$.

In addition, for example, the spectroscopic spectrum (also referred to as a first object spectroscopic spectrum) $L_{Sample}(\lambda_{G\_m}(k))$ of the colorimetric object 100 can be obtained by applying the first output signal $C_m(k)$ acquired by measurement using the first spectrocolorimetric device $1m$ for the colorimetric object 100 to Mathematical Formula (7). Then, the second object spectroscopic spectrum $L_{Sample}(\lambda^*_{G\_t}(k))$ can be acquired by the interpolation operation of the first object spectroscopic spectrum $L_{Sample}(\lambda_{G\_m}(k))$.

On the other hand, in some cases, the second estimated spectral reflectance $R^*(\lambda^*_{G\_t}(k))$ represented by Mathematical Formula (13) may be deviated from the actually measured value (also referred to as the second measured spectral reflectance) $R(\lambda^*_{G\_t}(k))$ of the second spectral reflectance calculated from the spectroscopic spectrum $L(\lambda^*_{G\_t}(k))$ obtained by actual measurement using the second spectrocolorimetric device $1t$. The difference between the second estimated spectral reflectance $R^*(\lambda^*_{G\_t}(k))$ and the second measured spectral reflectance $R(\lambda^*_{G\_t}(k)$ is estimated to be caused by the accuracy of wavelength calibration in the second spectrocolorimetric device $1t$.

Therefore, the calibrated spectral sensitivity $s^*_t(k,\lambda)$ in the second spectrocolorimetric device $1t$ is adjusted so as to minimize the difference between the second measured spectral reflectance $R(\lambda^*_{G\_t}(k))$ and the second estimated spectral reflectance $R^*(\lambda^*_{G\_t}(k))$.

Specifically, the calibrated spectral sensitivity $s^*_t(k,\lambda)$ that is provisionally set when the objective function F represented by Mathematical Formula (15) is included in a minimum region is estimated to be the calibrated spectral sensitivity $s^*_t(k,\lambda)$ relating to the second spectrocolorimetric device $1t$.

[Mathematical Formula 15]

$$F = \sum_{n=1}^{N_0} \sum_{k=1}^{K_0} (R_t * (\lambda^*_{G\_t}(k)) - R^*_t(\lambda^*_{G\_t}(k)))^2 \qquad (15)$$

Herein, the objective function F in Mathematical Formula (15) represents a summation of squares of differences between the second measured spectral reflectance $R(\lambda^*_{G\_t}(k))$ and the second estimated spectral reflectance $R^*(\lambda^*_{G\_t}(k))$ which are obtained for $N_0$ ($N_0$ is a natural number) samples. When the objective function F is included in the minimum region, the second estimated spectral reflectance $R^*(\lambda^*_{G\_t}(k))$ is matched with the second measured spectral reflectance $R(\lambda^*_{G\_t}(k))$. In addition, the state that the objective function F is included in the minimum region includes, for example, a state that the objective function F has a minimum value, a state that the objective function F has a value in the vicinity of the minimum value, and the like. The state that the objective function F has a value in the vicinity of the minimum value includes, for example, a state that, after the change of the objective function F is coarsely grasped, the objective function F is changed only by a preset predetermined value or less in slope in the vicinity of the minimum value. In addition, for example, a state that the difference between the second estimated spectral reflectance $R^*(\lambda^*_{G\_t}(k))$ and the second measured spectral reflectance $R(\lambda^*_{G\_t}(k))$ is included within a preset predetermined allowable range in which a color difference is about 0.1 or less may be the state that the objective function F is included in the minimum region.

If each of the $N_0$ samples exhibits a spectral reflectance in which the amount of change in the reflectance with respect to the change in the predetermined amount of wavelength exceeds a preset threshold value in the to-be-measured wavelength range, the second estimated spectral reflectance $R^*(\lambda^*_{G\_t}(k))$ can be matched to the second measured spectral reflectance $R(\lambda^*_{G\_t}(k))$. Namely, the calibrated spectral sensitivity $s^*_t(k,\lambda)$ can be easily and accurately set.

Figure 37:
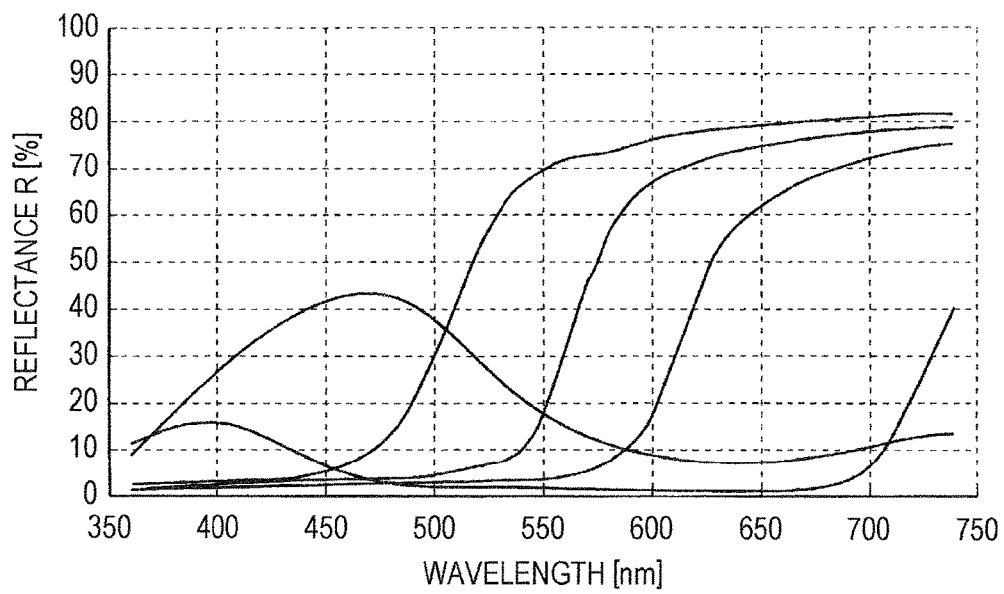
FIG. 37 is a diagram exemplifying spectral reflectances of a plurality of samples used for matching.

FIG. 37 is a diagram exemplifying the spectral reflectance of $N_0$ calibration samples used for matching. If the entire to-be-measured wavelength range is covered by a region where the spectral reflectance greatly changes in any of the $N_0$ calibration samples, the second estimated spectral reflectance $R^*(\lambda^*_{G\_t}(k))$ is accurately matched to the second measured spectral reflectance $R(\lambda^*_{G\_t}(k))$ in the entire to-be-measured wavelength range.

As illustrated in FIG. 37, if a plurality of calibration samples, for example, about five ($N_0$=5) calibration samples are used, the second estimated spectral reflectance $R^*(\lambda^*_{G\_t}(k))$ can be accurately matched to the second measured spectral reflectance $R(\lambda^*_{G\_t}(k))$ in the entire to-be-measured wavelength range of visible light. If the colorimetric object 100 is an object of a specific color, for example, one or more calibration samples of which spectral reflectance changes greatly in the wavelength range corresponding to the specific color may be used.

On the other hand, in order to allow the objective function F to be included in the minimum region, for example, while changing the calibrated spectral sensitivity $s^*_t(k,\lambda)$, it is necessary to obtain the objective function F of each provisional calibrated spectral sensitivity $s^*_t(k,\lambda)$.

Herein, it is assumed that the calibrated spectral sensitivity $s^*_t(k,\lambda)$ obtained by wavelength calibration in the second spectrocolorimetric device $1t$ for the k-th light-receiving element in the sensor unit 133 is a normal distribution function defined by the center wavelength $\lambda^*_{G\_t}(k)$ represented by the L-th order function of Mathematical Formula (16) and the full width at half maximum $\Delta\lambda^*_{FWHM}(k)$ represented by the L-th order function of Mathematical Formula (17). In addition, the order L may be, for example, a natural number of 2 or more.

[Mathematical Formula 16]

$$\lambda^*_{G\_t}(k) = a_L \cdot k^L + \ldots + a_0 \ldots \qquad (16)$$

[Mathematical Formula 17]

$$\Delta\lambda^*_{FWHM}(k) = b_L \cdot k^L + \ldots + b_0 \ldots \qquad (17)$$

Figure 38:
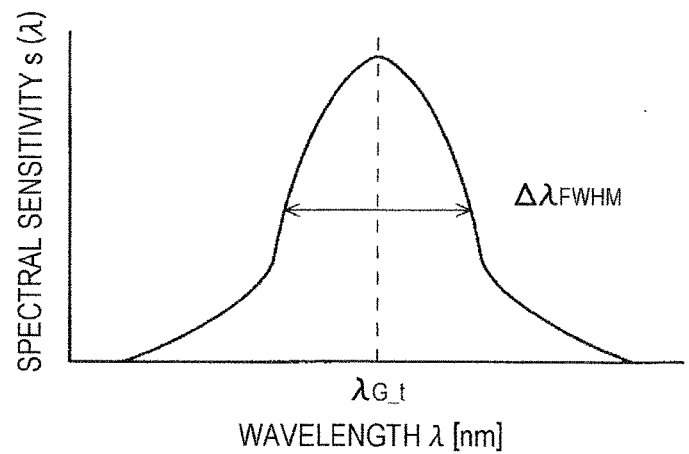
FIG. 38 is a diagram exemplifying a normal distribution function indicating a spectral sensitivity in one light-receiving element.

FIG. 38 is a diagram illustrating an example of the spectral sensitivity of the k-th light-receiving element.

In this case, in order to allow the objective function F defined by Mathematical Formula (15) to be included in the minimum region, for example, the coefficients $a_L, \ldots, a_0$ of Mathematical Formula (16) and the coefficients $b_L, \ldots, b_0$ of Mathematical Formula (17) may be obtained so that the objective function F is included in the minimum region. Specifically, for example, if L=2, six coefficients $a_2, a_1, a_0, b_2, b_1,$ and $b_0$ may be obtained. Then, if data based on the output from the light-receiving element at every 10 nm of 360 to 740 nm is obtained for one calibration sample, 195 points of data can be obtained for the five calibration samples. Of these, if there are a considerable number of data for the portion where the reflectance of the calibration sample is greatly changed, the values of the six coefficients $a_2, a_1, a_0, b_2, b_1,$ and $b_0$ of Mathematical Formulas (16) and (17) can be easily obtained.

From the above description, the second estimated spectral reflectance $R^*(\lambda^*_{G\_t}(k))$ is estimated from the first output signal $C_m(k)$ acquired by the first spectrocolorimetric device $1m$ by the following Steps i to v. Then, the following Steps i to v are repeated, and thus, the calibrated spectral sensitivity $s^*_t(k,\lambda)$ of the second spectrocolorimetric device $1t$ is obtained so that the second estimated spectral reflectance $R^*(\lambda^*_{G\_t}(k))$ and the second measured spectral reflectance $R(\lambda^*_{G\_t}(k))$ obtained by actual measurement using the second spectrocolorimetric device $1t$ are close to each other while the difference therebetween is included in the minimum region. Herein, the second estimated spectral reflectance $R^*(\lambda^*_{G\_t}(k))$ is calculated by using the spectroscopic spectrum measured by the light-receiving unit 13 of the first spectrocolorimetric device $1m$ for a calibration sample as one or more objects and the provisional calibrated spectral sensitivity $s^*_t(k,\lambda)$. In addition, the second measured spectral reflectance $R(\lambda^*_{G\_t}(k))$ is an actual measurement value of the spectral reflectance measured by the second spectrocolorimetric device $1t$ for the calibration sample as one or more objects. Then, the information indicating the calibrated spectral sensitivity $s^*_t(k,\lambda)$ obtained herein is stored in the storage unit 15 as the calibrated spectral sensitivity information S1.

[Step i] The center wavelength $\lambda^*_{G\_t}(k)$ and the full width at half maximum $4\lambda^*_{FWHM}(k)$ that define the calibrated spectral sensitivity $s^*_t(k,\lambda)$ of the k-th light-receiving element of the second spectrocolorimetric device $1t$ are provisionally determined. At this time, the coefficients $a_L, \ldots, a_0$ of Mathematical Formula (16) and the coefficients $b_L$, $b_0$ of Mathematical Formula (17) are provisionally determined. Accordingly, the inverse matrix of the calibrated spectral sensitivity $s^*_t(k,\lambda)$ of Mathematical Formula (12) is provisionally determined.

[Step ii] The luminance (first spectroscopic spectrum) $L(\lambda_{G\_m}(k))$ of the calibration sample is calculated on the basis of the first output signal $C_m(k)$ acquired by the first spectrocolorimetric device $1m$ and Mathematical Formula (7).

[Step iii] The second estimated output signal $C_t(k)$ that can be acquired by the second spectrocolorimetric device $1t$ is calculated by Mathematical Formula (10) on the basis of the first spectroscopic spectrum $L(\lambda_{G\_m}(k))$ obtained in Step ii, while the wavelength is being interpolated.

[Step iv] The second estimated spectroscopic spectrum $L^*(\lambda^*_{G\_t}(k))$ is calculated on the basis of the second estimated output signal $C_t(k)$ calculated in Step iii and Mathematical Formula (12) using the calibrated spectral sensitivity $s^*_t(k,\lambda)$ provisionally determined in Step i.

[Step v] The second estimated spectral reflectance $R^*_t(\lambda^*_{G\_t}(k))$ is calculated on the basis of the second estimated spectroscopic spectrum $L^*(\lambda^*_{G\_t}(k))$ calculated in Step iv and Mathematical Formula (13).

In this manner, the calibrated spectral sensitivity information S1 defining the second conversion rule for correcting the second deviation relating to the spectral sensitivity in order to convert the first spectral reflectance $R_m(\lambda)$ to the second spectral reflectance $R_t(\lambda)$ is set. Namely, in the case where such a configuration is employed, the deviation between the first spectral reflectance and the second spectral reflectance is treated to be divided into the first deviation relating to the linearity and the second deviation relating to the spectral sensitivity, and the second conversion rule is set by using limited calculation such as Mathematical Formulas (7), (10), (12), (13), and the like. Therefore, the second conversion rule can be set by using a relatively small number of calibration samples. Namely, a highly-accurate conversion rule of measurement values between the different first and second spectrocolorimetric devices $1m$ and $1t$ can be easily set.

Then, the second estimated spectral reflectance $R^*_t(\lambda^*_{G\_t}(k))$ that is estimated to be acquired by the second spectrocolorimetric device $1t$ can be calculated by using the first spectroscopic spectrum measured by the light-receiving unit 13 of the first spectrocolorimetric device $1m$ and the calibrated spectral sensitivity as the second conversion rule.

Figure 39:
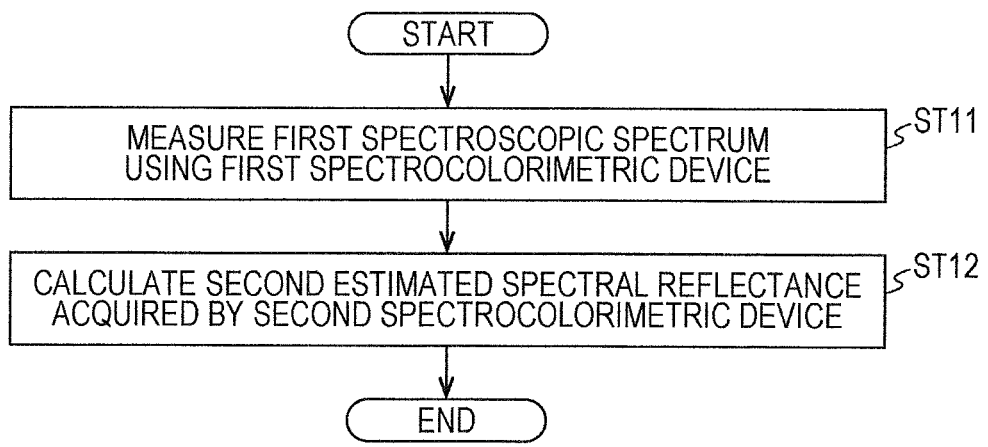
FIG. 39 is a flowchart illustrating an operation flow of converting a spectroscopic spectrum obtained by measurement using a first spectrocolorimetric device into a spectral reflectance that can be acquired by a second spectrocolorimetric device.

FIG. 39 is a flowchart illustrating an operation flow of correcting the second deviation relating to the spectral sensitivity.

First, in step ST11, the light-receiving unit 13 of the first spectrocolorimetric device $1m$ spectroscopically disperses the reflected light generated on the surface of the colorimetric object 100 according to the irradiation of the colorimetric object 100 with the illumination light emitted from the light source 11, so that the first spectroscopic spectrum $L(\lambda_{G\_m}(k))$ of the reflected light is measured. Herein, for example, the calculation unit $14ma$ calculates the first spectroscopic spectrum $L(\lambda_{G\_m}(k))$ of the colorimetric object 100 on the basis of the first output signal $C_m(k)$ acquired by the first spectrocolorimetric device $1m$ for the colorimetric object 100.

Next, in step ST12, the conversion unit $14mc$ of the first spectrocolorimetric device $1m$ calculates the second estimated spectral reflectance $R^*_t(\lambda^*_{G\_t}(k))$ that can be acquired by the second spectrocolorimetric device $1t$. Herein, for example, the second estimated spectral reflectance $R^*_t(\lambda^*_{G\_t}(k))$ is calculated from the first spectroscopic spectrum $L(\lambda_{G\_m}(k))$ by using the calibrated spectral sensitivity information S1 stored in the storage unit 15 and the first spectroscopic spectrum $L(\lambda_{G\_m}(k))$ measured in step ST11.

In the case where such a configuration is employed, since the calibrated spectral sensitivity for the second deviation relating to the spectral sensitivity is set separately from the first deviation relating to the reflectance, a highly-accurate conversion rule of measurement values between the different first and second spectrocolorimetric devices $1m$ and $1t$ can be easily set.

(2) Modified Example

In addition, the present invention is not limited to the above-described embodiment, and various modifications, improvements, and the like can be made without departing from the spirit of the present invention.

For example, in the above-described embodiment, in order to set the relationship information A1 for correcting the first deviation relating to the linearity between the devices, as an colorimetric object 100 having spectral reflectance, of which reflectance is substantially constant irrespective of the wavelength of the light, an achromatic calibration sample is used, but the present invention is not limited thereto. For example, at least a portion of the plurality of achromatic calibration samples having different spectral reflectances from each other may be replaced with a chromatic calibration sample of which reflectance is included within a width of the predetermined value range in a portion of the to-be-measured wavelength range to be measured by the first spectrocolorimetric device $1m$. Namely, for example, a mode may be employed where all of the plurality of calibration samples used for setting the relationship information A1 for correcting the first deviation relating to the linearity between the devices are calibration samples of which reflectance is included within a width of a predetermined value range in a portion of the to-be-measured wavelength range. At this time, for example, among the plurality of calibration samples, all the calibration samples may be achromatic, some calibration samples may be achromatic, or all the calibration samples may not be achromatic.

In the case where such a mode is employed, a plurality of calibration samples for obtaining the relationship between the reflectance and the reflectance difference for each wavelength can be easily prepared. Therefore, the relationship between the reflectance and the reflectance difference for each wavelength can be easily obtained.

In addition, the plurality of calibration samples employed for setting the relationship information A1 may include different calibration samples of which the reflectances in at least a portion of the to-be-measured wavelength range are within a width of a preset predetermined value range. However, in the case of employing such a configuration, for a calibration sample of which reflectance is included within a width of a preset predetermined value range only in a portion of the to-be-measured wavelength range can be employed to obtain the relationship between the first spectral reflectance $R_m(\lambda)$ and the reflectance difference $\Delta R(\lambda)$ for the portion of the wavelength range. For example, with respect to the red calibration sample illustrated in FIG. 4, the spectral reflectance can be substantially constant within a width of the predetermined value range in the range of 550 nm or less in the to-be-measured wavelength range. Therefore, the red calibration sample may be employed as a calibration sample to obtain the relationship between the first spectral reflectance $R_m(\lambda)$ and the reflectance difference $\Delta R(\lambda)$ in the range of 550 nm or less. Even in the case where such a configuration is employed, the relationship between the first spectral reflectance $R_m(\lambda)$ and the reflectance difference $\Delta R(\lambda)$ as a deviation component relating to the first spectral reflectance $R_m(\lambda)$ for each wavelength is easily acquired. Namely, a highly-accurate conversion rule of measurement values between the different first and second spectrocolorimetric devices $1m$ and $1t$ can be more easily set.

In addition, in the above-described embodiment, the case where, due to a difference in optical system such as retroreflection by the transparent member $17t$ between the first and second spectrocolorimetric devices $1m$ and $1t$, the reflectance difference can be generated between the first spectral reflectance $R_m(\lambda)$ and the second spectral reflectance $R_t(\lambda)$ is exemplified, but the present invention is not limited thereto. For example, the method of correcting the first deviation relating to the linearity according to the above-described embodiment may also be applied to the correction of the first deviation relating to the linearity caused by the deviation of the relationship between the amount of incident light and the output due to the difference in the characteristics of the light-receiving element of the light-receiving unit 13, the amplifier circuit, and the like between the first and second spectrocolorimetric devices $1m$ and $1t$.

Figure 40:
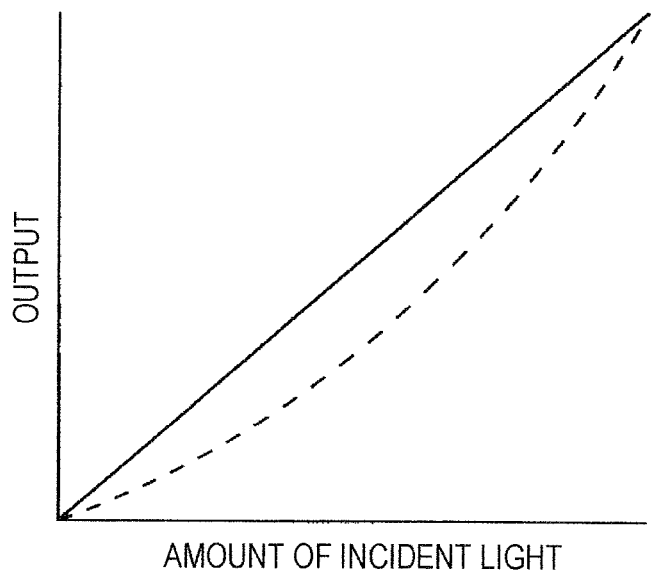
FIG. 40 is a diagram exemplifying a relationship between an amount of incident light and an output in first and second spectrocolorimetric devices.

FIG. 40 is a diagram exemplifying the relationship between the amount of incident light and the intensity of an output signal in each of the first and second spectrocolorimetric devices $1m$ and $1t$. In FIG. 40, the relationship between the amount of incident light and the intensity of an output signal in the first spectrocolorimetric device $1m$ is drawn by a solid line, and the relationship between the amount of incident light and the intensity of an output signal in the second spectrocolorimetric device $1t$ is drawn by a broken line.

In addition, in the above-described embodiment, the first and second spectrocolorimetric devices $1m$ and $1t$ are different types of devices, but the present invention is not limited thereto. For example, the first and second spectrocolorimetric devices $1m$ and $1t$ may be different devices of the same model. In other words, the method of correcting the first deviation relating to the linearity in the above-described embodiment may also be applied to the correction of the first deviation relating to the linearity occurring between the first and second spectrocolorimetric devices $1m$ and $1t$, which are different devices of the same model.

Figure 41:
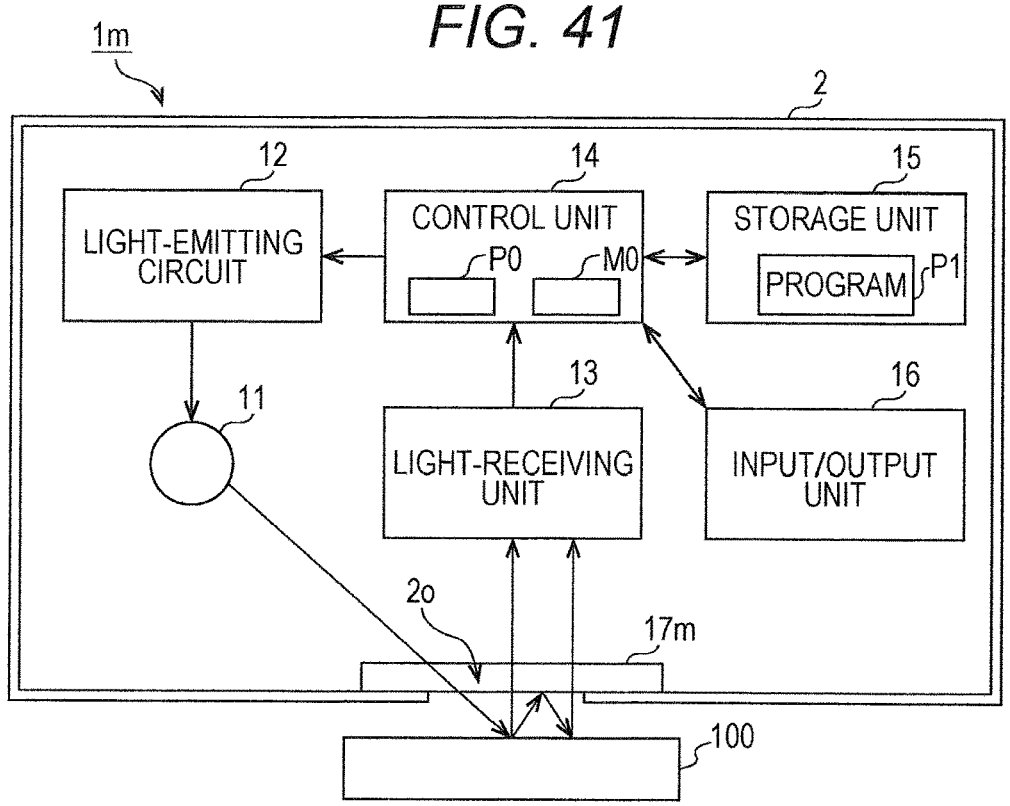
FIG. 41 is a diagram schematically illustrating a configuration example of a first spectrocolorimetric device.
Figure 42:
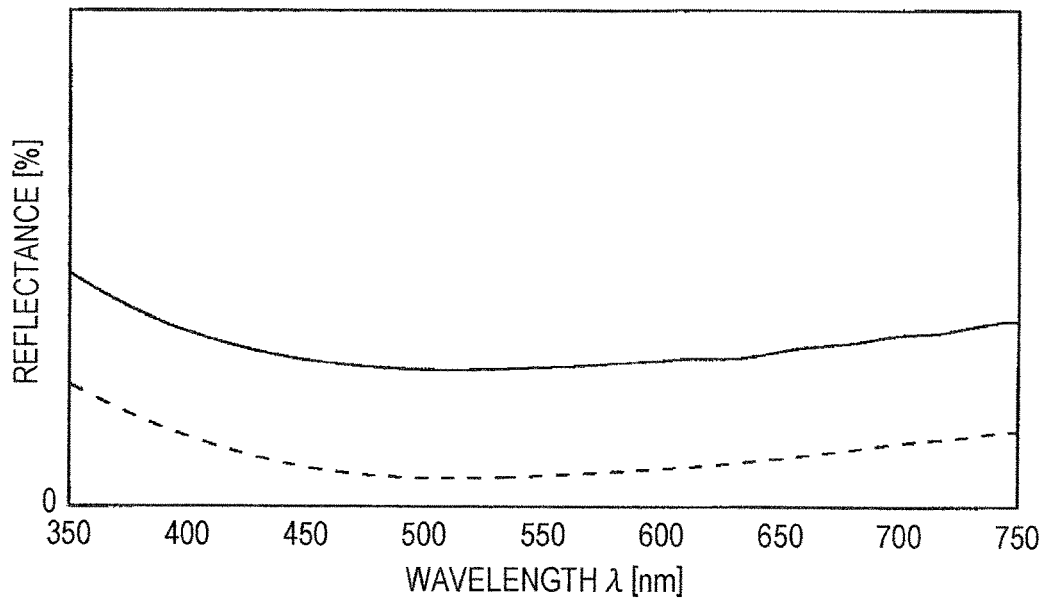
FIG. 42 is a diagram exemplifying spectral reflectances of two types of transparent members.

For example, as illustrated in FIG. 41, the case is assumed where, the first spectrocolorimetric device $1m$ is also provided with a transparent member $17m$ having the same configuration and function as the transparent member $17t$ in the second spectrocolorimetric device $1t$ and the first spectrocolorimetric device $1m$ and the second spectrocolorimetric device $1t$ are different devices of the same model. In this case, as illustrated in FIG. 42, the spectral reflectance can be different between the transparent member $17m$ and the transparent member $17t$. In FIG. 42, for example, the spectral reflectance in the transparent member $17m$ is indicated by a solid line and the spectral reflectance in the transparent member $17t$ is indicated by a broken line. Namely, the spectral reflectances of the transparent members $17m$ and $17t$ or the like can have deviation for each of the transparent members $17m$ and $17t$. As a result, the mode of retroreflection may be different between the first and second spectrocolorimetric devices $1m$ and $1t$. As a result, with respect to the same colorimetric object 100, a deviation may occur between the first spectral reflectance $R_m(\lambda)$ acquired by measurement using the first spectrocolorimetric device $1m$ and the second spectral reflectance $R_t(\lambda)$ acquired by measurement using the second spectrocolorimetric device $1t$.

In addition, in the above-described embodiment, for example, the correction of the second deviation relating to the spectral sensitivity is described by using 14 formulas of Mathematical Formulas (4) to (17), but the present invention is not limited thereto. For example, at least a portion of 14 Mathematical Formulas (4) to (17) may be integrated or decomposed as appropriate to obtain one or more formulas. In addition, if the first and second spectrocolorimetric devices $1m$ and $1t$ are produced by the same manufacturer and the manufacturer has information on the wavelength calibration of each device, such a configuration may be employed where the second estimated spectral reflectance is calculated on the basis of the data obtained by the first spectrocolorimetric device $1m$ and the information relating to the wavelength calibration of the second spectrocolorimetric device $1t$ and the calibrated spectral sensitivity $s^*_t(k,\lambda)$ is obtained so that the summation of squares of differences between the second estimated spectral reflectance and the second measured spectral reflectance obtained by actual measurement using the second spectrocolorimetric device $1t$ is minimized.

In addition, in the above-described embodiment, the calibrated spectral sensitivity $s^*_t(k,\lambda)$ is a normal distribution function defined by a center wavelength $\lambda^*_{G_t}(k)$ indicated by an L-th order function represented by Mathematical Formula (16) and a full width at half maximum $\Delta\lambda^*_{FWHM_t}(k)$ indicated by an L-th order function represented by Mathematical Formula (17), but the present invention is not limited thereto. For example, the calibrated spectral sensitivity $s^*_t(k,\lambda)$ may be represented by a different formula such as a formula representing the calibrated spectral sensitivity by appropriately shifting the reference formula.

In addition, in the above-described embodiment, the true spectral sensitivity $s_m(k,\lambda)$ in the first spectrocolorimetric device $1m$ and the true spectral sensitivity $s_t(k,\lambda)$ in the second spectrocolorimetric device $1t$ are accurately acquired, but the present invention is not limited thereto. For example, even though some error occurs between the spectral sensitivity acquired by measurement using a bright-line light source or the like and the true spectral sensitivity $s_m(k,\lambda)$ or $s_t(k,\lambda)$, the objective function F defined by Mathematical Formula (15) is allowed to be included in the minimum region and the calibrated spectral sensitivity $s^*_t(k,\lambda)$ is calculated, so that the influence due to the slight error can be reduced. For this reason, even in the case where the first spectrocolorimetric device $1m$ is a product of a certain manufacturer and the second spectrocolorimetric device $1t$ is a product of another manufacturer, the calibrated spectral sensitivity information S1 defining the second conversion rule can be set at a good accuracy.

In addition, in the above-described embodiment, the coefficients $a_L, \ldots, a_0$ of Mathematical Formula (16) and the coefficients $b_L, \ldots, b_0$ of Mathematical Formula (17) are adjusted so that the objective function F of Mathematical Formula (15) is included in the minimum region, but the present invention is not limited thereto. For example, if the first and second spectrocolorimetric devices $1m$ and $1t$ are products of the same manufacturer and, in the manufacturer of the first and second spectrocolorimetric devices 1*m* and 1*t*, the true spectral sensitivity $s_m(k,\lambda)$ in the first spectrocolorimetric device 1*m* and the true spectral sensitivity $s_t(k,\lambda)$ in the second spectrocolorimetric device 1*t* are known, the calibrated spectral sensitivity $s^*_t(k,\lambda)$ determined by the calibration at the factory of the second spectrocolorimetric device 1*t* may be employed as the second conversion rule without changing the calibrated spectral sensitivity.

The "calibration at the factory" referred to herein may obtain, for example, the coefficients $a_L, \ldots, a_0$ of Mathematical Formula (16) and the coefficients $b_L, \ldots, b_0$ of Mathematical Formula (17) that define the calibrated spectral sensitivity $s^*_t(k,\lambda)$. Herein, the calibration at the factory can be performed in various methods. Specifically, for example, the coefficients $a_L, \ldots, a_0$ and $b_L, \ldots, b_0$ are set so that the measurement value of the spectroscopic spectrum acquired by measurement using the second spectrocolorimetric device 1*t* for monochromatic light having a very narrow full width at half maximum of a wavelength emitted from a bright-line light source or the like coincides with the spectroscopic spectrum of an actual monochromatic light. Namely, the calibrated spectral sensitivity $s^*_t(k,\lambda)$ is set as the calibration result.

In the case where such a configuration is employed, first, the first spectroscopic spectrum $L(\lambda_{G\_m}(k))$ is calculated from the first output signal $C_m(k)$ acquired by the first spectrocolorimetric device 1*m* for the colorimetric object 100 by Mathematical Formula (7). Next, by applying the first spectroscopic spectrum $L(\lambda_{G\_m}(k))$ and the spectral sensitivity $s_t(k,\lambda)$ to Mathematical Formula (10), the second estimated output signal $C_t(k)$ which can be acquired by the second spectrocolorimetric device 1*t* is calculated. Next, by applying the inverse matrix of the second estimated output signal $C_t(k)$ and the calibrated spectral sensitivity $s^*_t(k,\lambda)$ as the calibration result to Mathematical Formula (12), the second estimated spectroscopic spectrum $L^*(\lambda^*_{G\_t}(k))$ is calculated. Then, the second estimated spectral reflectance $R^*(\lambda^*_{G\_t}(k))$ can be calculated by applying the second estimated spectroscopic spectrum $L^*(\lambda^*_{G\_t}(k))$ to Mathematical Formula (13). Then, the calculation for allowing the objective function F to be included in the minimum region is unnecessary.

In addition, in the above-described embodiment, it is assumed that the spectroscopic spectrum of the irradiation light emitted from the light source 11 is constant, but the present invention is not limited thereto. For example, it is assumed that the spectroscopic spectrum of the irradiation light changes as time elapses. In this case, in the first spectrocolorimetric device 1*m*, the irradiation light may be directly received to acquire the output signal for reference, the output signals obtained with respect to the colorimetric object 100, the white calibration plate, and the black calibration plate may be divided by the acquired output signal for reference, and then, the spectral reflectance may be calculated by Mathematical Formulas (13), (14), or the like.

In addition, in the above-described embodiment, it is assumed that the relationship information A1 and the calibrated spectral sensitivity information S1 are set on the manufacturer side, but the present invention is not limited thereto. For example, on the user side, the relationship information A1 and the calibrated spectral sensitivity information S1 may be set. At this time, on the user side, the first and second spectrocolorimetric devices 1*m* and 1*t*, the plurality of achromatic calibration samples for correcting the first deviation relating to the linearity, and one or more chromatic calibration samples for correcting the second deviation relating to the spectral sensitivity are used. Specifically, for example, on the user side, measurement may be performed using the first and second spectrocolorimetric devices 1*m* and 1*t* for a plurality of achromatic calibration samples and one or more chromatic calibration samples, and the information obtained as a result may be described in the storage unit 15 as the relationship information A1 and the calibrated spectral sensitivity information S1. Accordingly, since the relationship information A1 and the calibrated spectral sensitivity information S1 are set by using the second spectrocolorimetric device 1*t* owned by the user, a highly-accurate conversion rule of the measurement value between the different first and second spectrocolorimetric devices 1*m* and 1*t* can be set.

In addition, in the above-described embodiment, in FIG. 1, FIG. 2 and FIG. 41, the configuration of 45/0 (45° illumination and vertical reception) recommended by the International Commission on Illumination (CIE) or the configuration of 0/45 (vertical illumination and 45° reception) recommended by the CIE has been employed, but the present invention is not limited thereto. For example, in the first and second spectrocolorimetric devices 1*m* and 1*t*, for example, other configurations such as a configuration where an integration sphere is provided between the light source 11, the opening 2*o*, and the light-receiving unit 13 may be employed.

All or a portion of the above-described embodiment and various modified examples can be combined as appropriate within a range without inconsistency.

REFERENCE SIGNS LIST

1*m* First spectrocolorimetric device
1*t* Second spectrocolorimetric device
2 Housing
2*o* Opening
11 Light source
12 Light-emitting circuit
13 Light-receiving unit
14 Control unit
14*ma*, 14*ta* Calculation unit
14*mb* Acquisition unit
14*mc* Conversion unit
14*md* Arithmetic unit
14*me* Setting unit
15 Storage unit
16 Input/output unit
17*m*, 17*t* Transparent member
100 Colorimetric object
131 Slit plate
132 Spectroscopic unit
133 Sensor unit
A1 Relationship information
S1 Calibrated spectral sensitivity information
L0 Incident light
M0 Memory
P0 Processor
P1, P2 Program

The invention claimed is:

1. A spectrocolorimetric device comprising:
   a light source;
   a light-receiver which spectroscopically disperses reflected light generated on a surface of an object according to irradiation of the object with illumination light emitted from the light source by a measurer of a line sensor and measures a spectroscopic spectrum of the reflected light;

a converter which calculates an estimate of a spectral reflectance that can be acquired by another spectrocolorimetric device different from the spectrocolorimetric device from the spectroscopic spectrum by using a calibrated spectral sensitivity of the other spectrocolorimetric device and the spectroscopic spectrum; and a controller which sets a coefficient defining a spectral sensitivity of each element of a line sensor of the other spectrocolorimetric device as a calibrated spectral sensitivity by adjusting the coefficient so that a difference between a spectral reflectance obtained by measuring the object by the other spectrocolorimetric device and the estimate of the spectral reflectance that can be acquired by the other spectrocolorimetric device and calculated by the converter becomes small, wherein the calibrated spectral sensitivity includes a provisional calibrated spectral sensitivity when a difference between the estimated value of the spectral reflectance that can be acquired by the other spectrocolorimetric device that is calculated by using the spectroscopic spectrum measured by the light-receiver and the provisional calibrated spectral sensitivity for one or more objects and an actually measured value of the spectral reflectance measured by the other spectrocolorimetric device for the one or more objects is included in a minimum region.

2. The spectrocolorimetric device according to claim 1, wherein a regulation of the spectral sensitivity depends on a function defining a center wavelength and a full width at half maximum of each element of the line sensor.

3. The spectrocolorimetric device according to claim 1, wherein the one or more objects exhibit the spectral reflectance in which an amount of change in reflectance with respect to a change in a predetermined amount of wavelength in a to-be-measured wavelength range exceeds a preset threshold.

4. The spectrocolorimetric device according to claim 1, further comprising:

a calculator which calculates a first spectral reflectance from the spectroscopic spectrum;

a storage which stores relationship information indicating a relationship between a reflectance and a reflectance difference as a deviation component of reflectance for each wavelength; and an acquirer which acquires reflectance difference for each wavelength between the first spectral reflectance acquired by measurement using the spectrocolorimetric device and an estimate of a second spectral reflectance that can be acquired by measurement using the other spectrocolorimetric device on the basis of the first spectral reflectance and the relationship information, wherein the converter calculates the estimated spectral reflectance that can be acquired by the other spectrocolorimetric device by adding or subtracting the reflectance difference for each wavelength acquired by the acquirer to or from the spectral reflectance acquired by using the spectroscopic spectrum and the calibrated spectral sensitivity.

5. A spectral reflectance calculating method comprising:

(a) in a light-receiver of a first spectrocolorimetric device, spectroscopically dispersing reflected light generated on a surface of an object according to irradiation of the object with illumination light emitted from a light source by a measurer of a line sensor and measuring a spectroscopic spectrum of the reflected light;

(b) in a converter of the first spectrocolorimetric device, calculating an estimate of a spectral reflectance that can be acquired by a second spectrocolorimetric device different from the first spectrocolorimetric device from the spectroscopic spectrum by using a calibrated spectral sensitivity of the second spectrocolorimetric device and the spectroscopic spectrum measured in (a); and (c) setting a coefficient defining a spectral sensitivity of each element of a line sensor of another spectrocolorimetric device as a calibrated spectral sensitivity by adjusting the coefficient so that a difference between a spectral reflectance obtained by measuring the object by the other spectrocolorimetric device and an estimate of the spectral reflectance that can be acquired by the other spectrocolorimetric device and calculated by the converter becomes small, wherein the calibrated spectral sensitivity includes a provisional calibrated spectral sensitivity when a difference between an estimated value of the spectral reflectance that can be acquired by the other spectrocolorimetric device that is calculated by using the spectroscopic spectrum measured by the light-receiver and the provisional calibrated spectral sensitivity for one or more objects and an actually measured value of the spectral reflectance measured by the other spectrocolorimetric device for the one or more objects is included in a minimum region.

6. The spectral reflectance calculating method according to claim 5, wherein a regulation of the spectral sensitivity depends on a function defining a center wavelength and a full width at half maximum of each element of the line sensor.

7. A spectrocolorimetric device comprising:

a light source;

a light-receiver which spectroscopically disperses reflected light generated on a surface of an object according to irradiation of the object with illumination light emitted from the light source by a measurer of a line sensor and measures a spectroscopic spectrum of the reflected light;

a converter which calculates an estimate of a spectral reflectance that can be acquired by another spectrocolorimetric device different from the spectrocolorimetric device from the spectroscopic spectrum by using a calibrated spectral sensitivity of the other spectrocolorimetric device and the spectroscopic spectrum; and a storage which stores a second conversion rule for correcting a deviation based on the spectral sensitivity of each element of the line sensor, wherein the storage further stores a first conversion rule for correcting a deviation based on a proportional relationship between an intensity of incident light incident on the line sensor and an intensity of light output from the line sensor.

* * * * *